US009200317B2

(12) United States Patent
Tisi et al.

(10) Patent No.: US 9,200,317 B2
(45) Date of Patent: Dec. 1, 2015

(54) NUCLEIC ACID AMPLIFICATION

(75) Inventors: Laurence Carlo Tisi, Cambridge (GB); Olga Gandelman, Cambridge (GB); Guy Kiddle, Cambridge (GB); Cathal McElgunn, Cambridge (GB)

(73) Assignee: LUMOR LIMITED, Cambridge (GB)

( * ) Notice: Subject to any disclaimer, the term of this patent is extended or adjusted under 35 U.S.C. 154(b) by 363 days.

(21) Appl. No.: 12/737,448

(22) PCT Filed: Jul. 13, 2009

(86) PCT No.: PCT/GB2009/001728
§ 371 (c)(1),
(2), (4) Date: Apr. 8, 2011

(87) PCT Pub. No.: WO2010/007355
PCT Pub. Date: Jan. 21, 2010

(65) Prior Publication Data
US 2011/0177513 A1 Jul. 21, 2011

(30) Foreign Application Priority Data
Jul. 14, 2008 (GB) .................................. 0812862.1

(51) Int. Cl.
C12Q 1/68 (2006.01)
C12P 19/34 (2006.01)

(52) U.S. Cl.
CPC .................................. C12Q 1/6848 (2013.01)

(58) Field of Classification Search
CPC ........... C12Q 1/6848; C12Q 2531/101; C12Q 2545/101; C12Q 2527/107; C12Q 2527/113
See application file for complete search history.

(56) References Cited

U.S. PATENT DOCUMENTS 5,882,857 A * 3/1999 Western et al. .............. 435/6.12
2006/0188911 A1 8/2006 Otomo et al.
(Continued)

FOREIGN PATENT DOCUMENTS

EP 1 493 822 1/2005
WO WO 00/14279 3/2000
(Continued)

OTHER PUBLICATIONS

Haugland et al., "Evaluation of different methods for the extraction of DNA from fungal conidia by quantitative competitive PCR analysis," Journal of Microbiological Methods, 1999, vol. 37, pp. 165-176.*
(Continued)

*Primary Examiner* — Young J Kim
(74) *Attorney, Agent, or Firm* — Nixon & Vanderhye P.C.

(57) ABSTRACT

A method for determining the presence and/or amount of a first polynucleic acid in a sample comprising subjecting the sample to nucleic acid amplification in which product is detectable by the presence of a signal generated by polynucleic acid formation from the first polynucleotide characterised in that the nucleic acid amplification reaction is conducted, in the same reaction vessel, with a predetermined amount of a second polynucleic acid which is subjected to nucleic acid amplification, the product of which is detectable by the presence of the same signal generated by polynucleic acid formation from the second polynucleotide as that generated by polynucleic acid formation from the first polynucleotide and wherein the product of the second polynucleic acid is produced with different reaction kinetics from the product of the first polynucleic acid such that the second polynucleic acid acts as an internal control for the method.

28 Claims, 18 Drawing Sheets

(56) References Cited

U.S. PATENT DOCUMENTS

2006/0292571 A1    12/2006  Babiel et al.
2010/0233715 A1*    9/2010  Yonekawa et al. ................ 435/6

FOREIGN PATENT DOCUMENTS

| WO | WO 2004/062338 | A2 | 7/2004 |
|----|----------------|-----|--------|
| WO | WO 2004/104229 |    | 12/2004 |
| WO | WO 2006/010948 |    | 2/2006 |
| WO | WO 2006/034215 | A2 | 3/2006 |
| WO | WO 2007/020384 |    | 2/2007 |

OTHER PUBLICATIONS

International Search Report for PCT/GB2009/001728, mailed Dec. 7, 2009.
Written Opinion of the International Searching Authority for PCT/GB2009/001728, mailed Dec. 7, 2009.
Sanchez, J.A. et al., "Linear-After-The-Exponential (LATE)-PCR: An advanced method of symmetric PCR and its uses in quantitative real-time analysis", Proceedings of the National Academy of Sciences of USA, vol. 101, No. 7, (Feb. 17, 2004), pp. 1933-1938.
European Search Report dated Dec. 1, 2008, issued in connection with GB 0812862.1.
Remarks filed Jun. 6, 2012 by Mr. Huw George Hallybone of Carpmaels & Ransford.
Office Action dated Feb. 7, 2013, issued in connection with European Patent Application No. 09 784 687.7.
Hoofar et al, "Practical Considerations in Design of Internal Amplification Controls for Diagnostic PCR Assays", Journal of clinical Microbiology 2004, 42(5):1863-1868.
EPO Communication dated Jul. 10, 2012 in European Patent Application No. 09 784 687.7.
EP Office Action dated Oct. 24, 2014, issued in connection with European Patent Application No. 09 784 687.7.
Corey et al, "Improved reverse transcriptase-polymerase chain reaction protocol with exogenous internal competitive control for prostate-specific antigen mRNA in blood and bone marrow", Clinical Chemistry 43:3, pp. 443-452 (1997).

* cited by examiner

FIG. 1(a)

Equation for Richards' curve: $Y = A + \dfrac{C}{(1 + Te^{-B(X-M)})^{1/T}}$

Y: = Nucleic acid synthesized during amplification
X: = Time
A: = lower asymptote
C: = upper asymptote
M: = time to maximal rate of nucleic acid synthesis
B: = Amplification rate
T: = affects near which asymptote the maximal rate of nucleic acid synthesis occurs

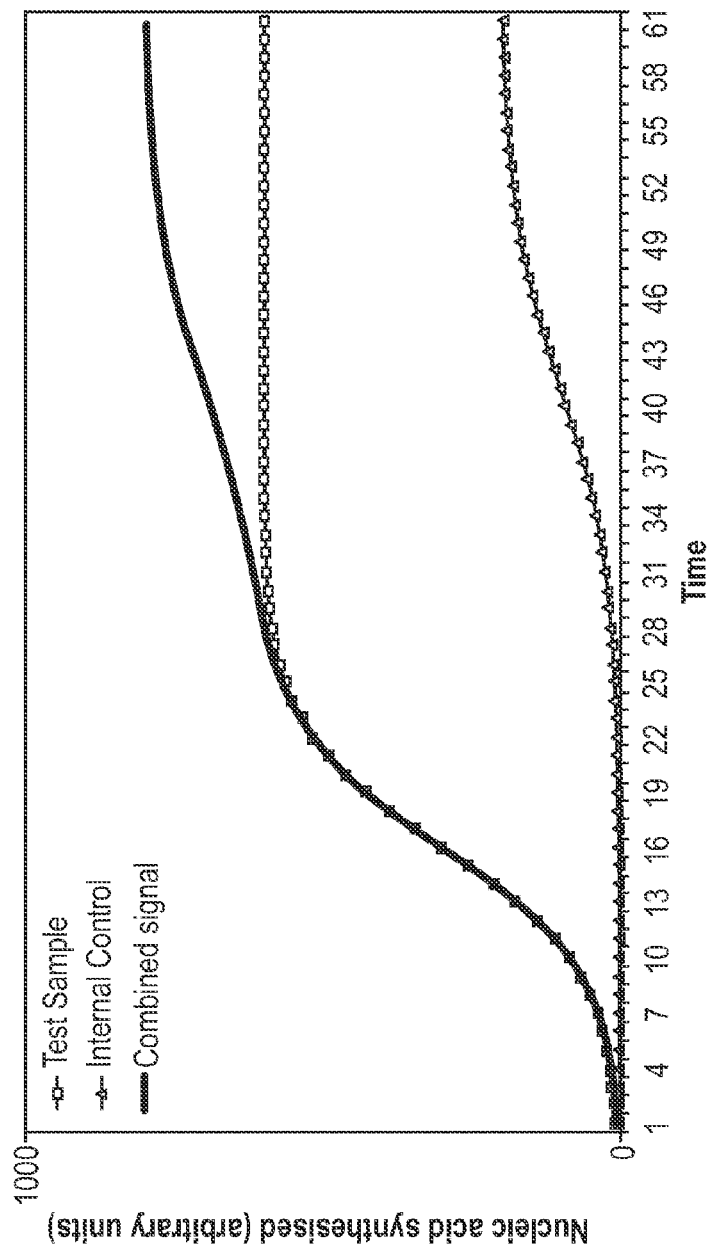

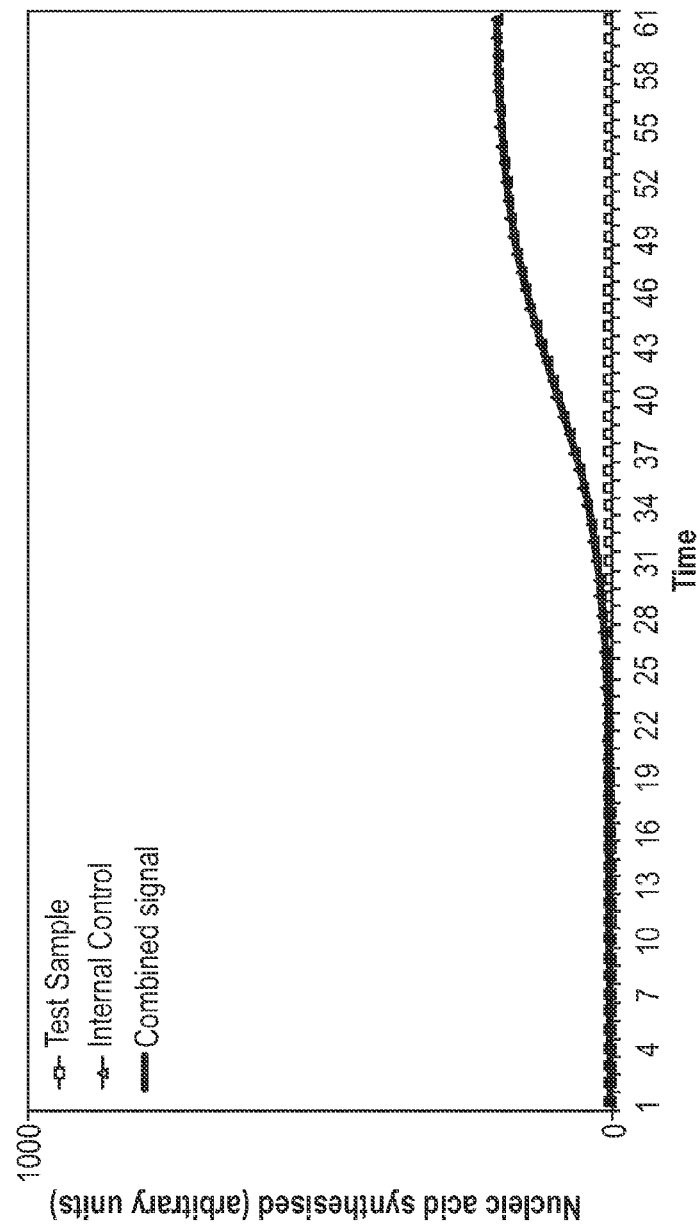

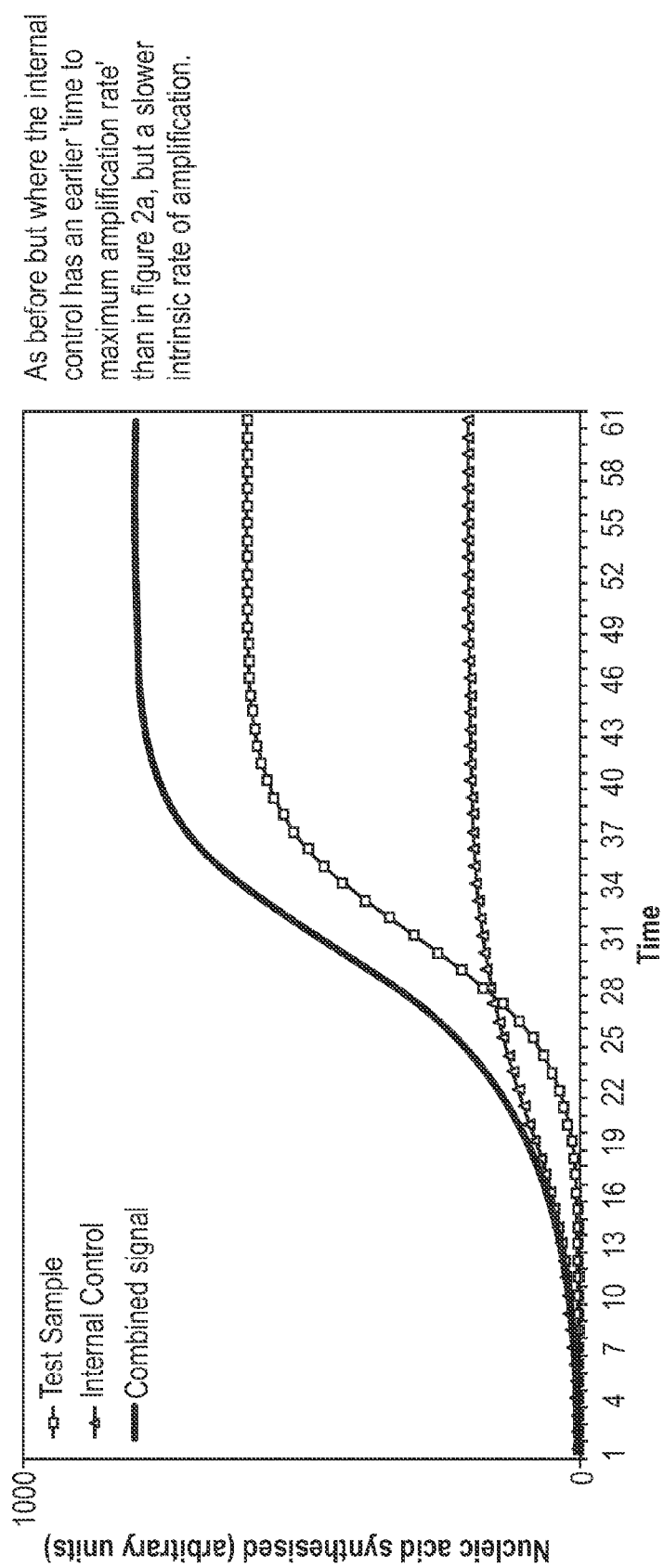

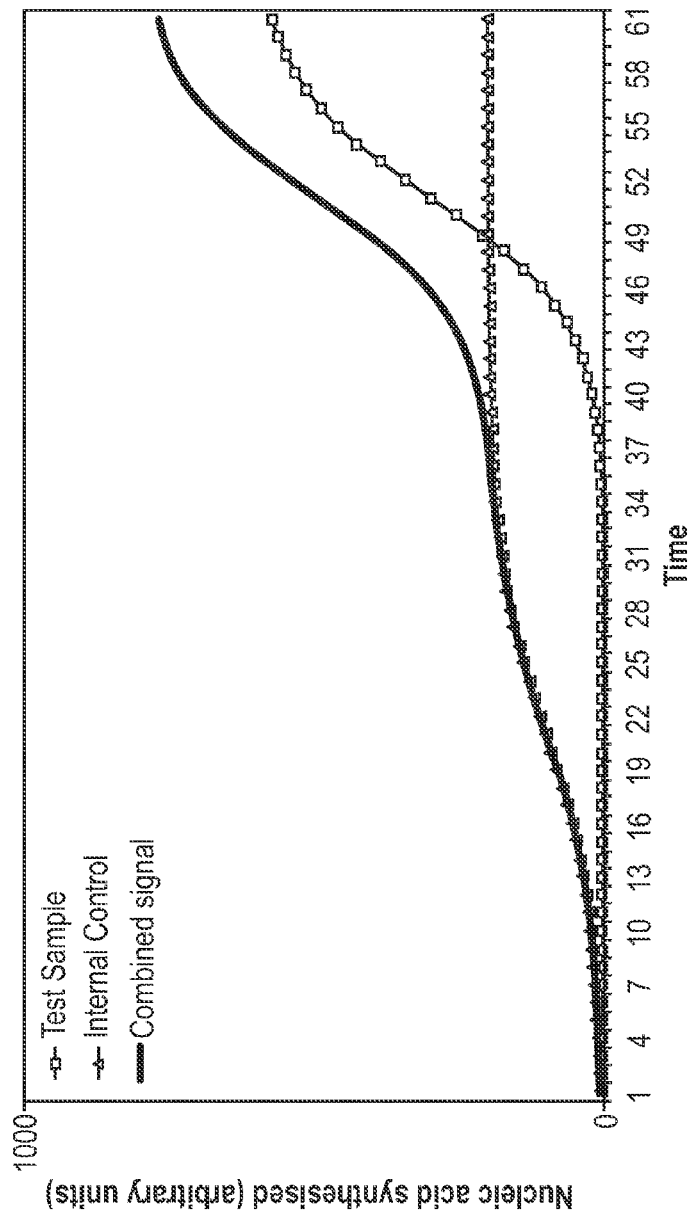

— Exponential/Fast   — — Linear/Slow

— 1. Strong pos, no inhib    ······ 2. Strong pos, with inhib
— — 3. Weak pos, no inhib    - - - - 4. Weak pos, with inhib
— — 5. NTC, no inhib         ········ 6. NTC, with inhib

NUCLEIC ACID AMPLIFICATION

This application is the U.S. national phase of International Application No. PCT/GB2009/001728 filed 13 Jul. 2009, which designated the U.S., and claims priority to GB Application No. 0812862.1 filed 14 Jul. 2008, the entire contents of which is hereby incorporated by reference.

FIELD OF THE INVENTION

The present invention relates to the field of nucleic acid amplification. In particular, it relates to a method for specific amplification and detection of a test sample and an internal control in the same reaction vessel.

BACKGROUND

Nucleic acid amplification technology (NAAT) is an invaluable and powerful tool in many areas of research and diagnosis. Such NAAT techniques allow detection and quantitation of a nucleic acid in a sample with high sensitivity and specificity as well as quantitative analysis of nucleic acids in a sample.

Nucleic acid amplification may be used to determine the presence of a particular template nucleic acid in a sample, as indicated by the presence of an amplification product following the implementation of a particular NAAT. Conversely, the absence of any amplification product indicates the absence of template nucleic acid in the sample. Such techniques are of great importance in diagnostic applications, for example, for determining whether a pathogen is present in a sample.

The prior art has described a variety of thermocycling and isothermal techniques for amplification of nucleic acids. Thermocycling techniques, such as the polymerase chain reaction (PCR), use temperature cycling to drive repeated cycles of DNA synthesis leading to large amounts of new DNA being synthesised in proportion to the original amount of template DNA. A number of isothermal techniques have also been developed that do not rely on thermocycling to drive the amplification reaction. Isothermal techniques, which utilise DNA polymerases with strand-displacement activity, have been developed for amplification reactions that do not involve an RNA-synthesis step. Similarly, for amplification reactions that do involve an RNA-synthesis step, isothermal techniques have been developed that may use reverse transcriptase, RNase H and/or a DNA-dependent RNA polymerase (see for example, Nucleic Acid Isothermal Amplification Technologies—A Review. Nucleosides, Nucleotides and Nucleic Acids, Volume 27, Issue 3 Mar. 2008, pages 224-243).

One thing all NAAT techniques have in common is that it is often essential that the reaction is monitored by suitable controls in order to ensure that a negative result is actually due to the absence of the nucleic acid rather than due to other factors, for example the presence of inhibitors in a sample. The prior art describes several methods to achieve this.

One method is to perform two amplification reactions in separate vessels in parallel. One vessel contains the test sample and the other contains a nucleic acid of a known sequence, which serves as a positive control, in addition to the test sample. If no amplification is detected in the test sample but an amplification product can be detected in the control sample, the test can be considered true negative. Likewise, if no amplification product is present in the control, an inhibitor must be present in the sample.

The use of an internal control, i.e. a control which is amplified in the same reaction vessel, has some advantages over using two vessels to establish whether inhibitors are present. Firstly, fewer tubes and reagents are required, thereby reducing the unit cost per test where an inhibitor control is absolutely required. Secondly, fewer manipulations are required. Thirdly, since fewer tubes are required, more samples can be analysed per unit capacity of the hardware used to run the reaction. For example, using a standard 96 well detection system, 96 samples can be analysed using an internal control whereas only 48 samples can be analysed where two vessels must be used per test.

The internal control method presents the technical challenge of differentiating between the signal resulting from the target polynucleotide in the sample and the signal resulting from the control nucleic acid. To detect the signals from a sample and the control nucleic acid in the same vessel, it is necessary that the sequence of the control nucleic acid has some associated difference from the target nucleic acid to allow a detection system to differentiate between the two amplified products. Further still, there needs to be some means to differentiate the respective signals from the two amplification processes. This has been achieved by the use of separate reporter systems for the test-sample and control respectively. For example, two fluorescent probes may be employed of different emission maxima (or different enough for their respective signals to be differentiated) one which only gives a signal on binding to the products of the test-sample amplification process, and one which only gives a signal when binding to the products of the control products. In this way, by detecting two independent signals from a sample, it is possible to follow the respective amplification processes in the same reaction vessel.

Alternatively, where appropriate, a melt-curve analysis of the results of an amplification reaction can be performed to assess if there is signal from the test-sample and control. This may or may not encompass the use of fluorescent probes (see, for example EP1109934). The test-sample and the control are thereby amplified with the same reaction kinetics. The disadvantage of the melt-curve analysis is that it requires an additional step after the amplification reaction in order to detect the control which does not only elongate the process but also adds significant complexity to the hardware which is required to detect the control and the amplified polynucleic acid.

Where two or more reporter systems must be employed, the hardware used to detect the reporter must be sophisticated enough to perform measurements and differentiate at least two reporter signals. Further, for practical applications in diagnostics, these readings must be performed on a small sample, or multiple small samples: typically reactions volumes are between 10-100 µl to avoid high reagent costs per test. This requires very sophisticated hardware which is very expensive.

Hence, there is a need in the art for improved detection methods for detection of nucleic acids and internal controls in the same reaction vessel. In particular, a method whereby an internal control could be monitored without the need for two separate reporter signals to be independently measured, would be of great benefit as this would omit the necessity for expensive hardware that can measure multiple signals following NAAT. Furthermore there are some NAAT techniques which utilize reporter technologies whereby it is not possible to measure more than one type of signal from a sample. Such methods include reporter systems based on bioluminescence (published International patent applications WO 2004/062338 & WO 2006/010948), turbidity (published International patent application WO 01/83817) or certain electrochemical methodologies.

SUMMARY OF THE INVENTION

The invention provides a method for specific amplification and detection of a polynucleic acid and an internal control in the same reaction vessel.

Therefore, in one embodiment the present invention provides a method for determining the presence and/or amount of a first polynucleic acid in a sample comprising subjecting the sample to nucleic acid amplification in which product is detectable by the presence of a signal generated by polynucleic acid formation from the first polynucleotide characterised in that the nucleic acid amplification reaction is conducted, in the same reaction vessel, with a predetermined amount of a second polynucleic acid, the product of which is detectable by the presence of the same signal generated by nucleic acid formation from the second polynucleotide as that generated by polynucleic acid formation from the first polynucleotide and wherein the product of the second polynucleic acid is produced with different reaction kinetics from the product of the first polynucleic acid such that the second polynucleic acid acts as an internal control for the method.

In this specification the term "first polynucleic acid" is used interchangeably with "test-sample" and "target polynucleotide".

The nucleic acid amplification product is detectable by the presence of a signal generated by polynucleic acid formation. The signal may be generated from the product of amplification directly (e.g. by detecting polynucleic product generated by nucleic acid amplification) or the signal may be generated from by-products of the amplification (e.g. by detecting products which are produced during the process of amplification).

The underlying principle of the invention is the recognition that an internal control does not necessarily need to be involved in exactly the same amplification process as that of the test-sample. Rather, both the test-sample and standard need only share the same vessel and amplification reagents but not necessarily exactly equivalent amplification processes. Thus, it is possible to distinguish the amplification products from the target nucleic acid and the control.

In this way, it is possible to combine in a single vessel two amplification reactions which have different kinetics of amplification. Where the two amplification methods have sufficiently differing reaction kinetics it is possible, from a set of readings of signal against time, to resolve signals resulting from amplification of the test sample, from amplification resulting from the internal control. The respective signals from the two amplification processes may vary, for example, in respect of their maximal signal magnitude. In this way, an effective internal control is accomplished that can be analysed on hardware far simpler than fluorescent methods which require two signals to be measured from the vessel.

A method according to the invention may be practised with any NAAT known in the art in which the amplification product is detectable by the presence of a signal generated by polynucleic acid formation.

Some NAAT techniques require that the sample temperature is cycled between different temperatures in order to achieve amplification of a target nucleic acid sequence. Examples of such methods are Polymerase Chain Reaction (PCR, U.S. Pat. No. 4,683,202) and Ligase Chain Reaction (LCR; U.S. Pat. No. 5,185,243). Other NAATs may operate substantially at a single temperature. Of these some are dependent on transcription as part of the amplification process, for example Nucleic Acid Sequence Based Amplification (NASBA; U.S. Pat. No. 5,409,818) and Transcription Mediated Amplification (TMA; U.S. Pat. No. 5,399,491) while others are dependent on the action of a Helicase or Recombinase for example Helicase Dependent Amplification (HDA; WO2004027025) and Recombinase polymerase amplification (RPA; WO03072805) respectively, others still are dependent on the strand displacement activity of certain DNA polymerases, for example Strand Displacement Amplification (SDA; U.S. Pat. No. 5,455,166), Loop-mediated Isothermal Amplification (LAMP; WO 00/28082, WO 01/34790), Chimeric Displacement Reaction (RDC) (WO9794126), Rolling Circle Amplification (RCA; Lizardi, P. M. et al. Nature Genetics, (1998) 19.225-231), Isothermal Chimeric Amplification of Nucleic Acids (ICAN; WO0216639), SMart Amplification Process (SMAP; WO2005063977).

The methods used for amplification of the target nucleic acid and the control may be the same or different.

In one embodiment of the invention the internal control is amplified using an exponential nucleic acid amplification whilst the test-sample is amplified using a non-exponential, amplification process. However, in a preferred embodiment it is the internal control that is amplified using a non-exponential nucleic acid amplification and the test-sample using an exponential nucleic acid amplification. This is preferred because there is less chance of the amplification associated with the internal control, out-competing that of the test-sample.

Examples of exponential NAATs which can be used in accordance with the embodiments of the present invention include, but are not limited to, polymerase chain reaction, SDA, LAMP, ICAN, SMAP, RDC, (exponential)-RCA, NASBA, TMA, HDA and RPA.

Examples of non-exponential NAATs which can be used in accordance with the embodiments of the present invention include, but are not limited to Rolling circle amplification, asymmetric PCR, asymmetric LAMP (Isolation of single-stranded DNA from Loop-Mediated Isothermal Amplification (LAMP) products. Kentaro Nagamine, Yoko Kuzuhara et al. Biochemical and Biophysical Research Communications, Vol. 290, No. 4, 1195-1198, 2002) or any of the aforementioned exponential NAATs performed under conditions that affect the ability of the amplification process to successfully re-copy copies of the original template polynucleic acid.

The invention does not strictly require that the internal control be amplified by a non-exponential (e.g. linear) amplification process and the test-sample by an exponential process. Rather, it is only necessary that the kinetics and/or signal amplitudes associated with the respective amplification reactions differ significantly. Therefore, in a further embodiment, the invention provides a method wherein the first nucleic acid and the internal control are amplified using exponential nucleic acid amplification and wherein the two amplification reactions have different reaction kinetics, i.e. where the two reactions have fundamentally different kinetic description (i.e. where a different mathematical description is necessary to describe the internal control kinetics compared to the test-sample, for example where one process is linear and the other is exponential). In this embodiment, it is necessary to be able to ascertain, from a negative sample, that the signal from the internal control is not, in fact, a signal from the test-sample. For example, these different reaction kinetics may be achieved by virtue of the signal from the internal control a) having a smaller or bigger amplitude than the test sample
    b) having a longer or shorter lag-time before maximal amplification
    c) having a slower or faster intrinsic rate of amplification, or The above features allow mathematical algorithms to analyse a set of signal readings against time to ascertain whether the signal encompasses that of positive sample, a signal from the internal control alone or no signal from either the test-sample or the internal control (as would happen in the presence of an inhibitor).

For example, with reference to i) above, an algorithm could be employed to check whether the signal ever reached an amplitude of $A_{IS}$, associated with the expected amplitude from the internal control. If the amplitude failed to achieve an amplitude of $A_{IS}$ this would then be associated with inhibition of the sample. If the amplitude was greater than $A_{IS}$, the signal would be expected to stem from the test sample. "Greater than X" thereby means that the amplitude is at least 1.2 times, 1.5 times, 1.8 times, 2 times, 2.5 times, 3 times, 3.5 times, 4 times, 4.5 times, 5 times, 6 times, 7 times, 8, times, 9 times, 10 times, 20 times, 30 times, 40 times, 50 times or even 100 times bigger than the amplitude of the internal control. The value of $A_{IS}$ can thereby be easily determined by performing the method of the invention without the first polynucleic acid.

Similarly, with reference to ii) above, an algorithm could be employed to check whether a signal of particular amplitude was achieved at time $T_{IS}$, which would be solely associated with a signal from the internal control, or whether a signal of a particular amplitude was not achieved until after time $T_{IS}$, which would be associated with an inhibited sample. If a signal of a particular amplitude was achieved before time $T_{IS}$, this would be associated with a signal from the test sample.

Further, with reference to iii) above, an algorithm could be employed to check whether the rate of change of a signal achieved a predetermined amount $\Delta S_{IS}$ associated solely with signal from an internal control, whether the rate of change of signal failed to exceed $\Delta S_{IS}$ associated with an inhibited sample or whether the signal was greater than $\Delta S_{IS}$, which would then be associated with a signal from a positive sample. "Greater than $\Delta S_{IS}$" thereby means that the rate of change of a signal is at least 1.2 times, 1.5 times, 1.8 times, 2 times, 2.5 times, 3 times, 3.5 times, 4 times, 4.5 times, 5 times, 6 times, 7 times, 8, times, 9 times, 10 times, 20 times, 30 times, 40 times, 50 times or even 100 times greater than the rate of change of the internal control. The value of $\Delta S_{IS}$ can thereby be easily determined by performing the method of the invention without the first polynucleic acid.

Further, an algorithm could be employed to fit the signal generated from a sample to particular kinetic models to ascertain which kinetic description best fitted the data. For example, if the rate of change of signal fitted to an exponential rate equation with a better fit than a linear rate equation then the signal may be assigned to the amplification of target polynucleic acid in the test-sample rather than the internal control, whereas if the signal had been best fitted to a linear rate equation then the signal could be assigned to the internal control, if the signal approximates a straight line of zero gradient, then the signal could be assigned to be that from an inhibited sample. Suitable algorithms will be evident to those of skill in the art.

There is a variety of ways in which the kinetics of amplification processes can vary. For example, the kinetics of amplification can be described by a) the rate constant of amplification b) the time to reach maximal amplification c) the starting and final amplitudes of the measured parameter (i.e. the upper and lower asymptotes of the curve) and d) whether the amplitude of the signal at the time of maximal amplification is nearer the upper or lower asymptote. Such a description of a kinetic curve is known as Richards' Curve (see FIG. 1). However, a variety of other means to describe and differentiate between two different kinetic processes can also be envisaged other than that described by Richards' Curve.

Different kinetics of amplification can be achieved in various ways. In one embodiment of the invention, an internal control is provided wherein the binding sites for the primers used to exponentially amplify the polynucleotide sequence of interest are either partially absent or non-optimal in the control. Various examples of how such an internal control can be designed are shown in FIG. 10. For example in methods which require two primer binding sites (A and B) for exponential amplification (for example polymerase chain reaction, strand displacement amplification and Isothermal Chimeric Amplification of Nucleic Acids) different kinetics can be achieved by the following means:

only one of the primer binding sites (A or B) is present on the internal control both primer binding sites are present but more separated in sequence compared to the target polynucleotide. "More separated" thereby means that the distance between the two primers is bigger by at least 10 nucleotides, 50 nucleotides, 100 nucleotides, 500 nucleotides, 1000 nucleotides or even 5000 nucleotides.

both primer binding sites are present but separated by a region which is slower for a polymerase to copy compared to the target polynucleotide.

both primer binding sites are present but either one or both of the primer sites contain miss-matches that cause amplification to occur less efficiently one or both primer binding sites are present on a circular polynucleic acid molecule but in an orientation that prevents exponential amplification All these examples could result in amplification kinetics for the internal control that are distinguishable from the exponential process amplifying the target polynucleic acid and are therefore an embodiment of the present invention. This approach does not require any additional reagents to be present in the amplification mix other than the internal control polynucleic acid; therefore it is facile to envisage how it is possible to accommodate both the amplification of the test sample and the amplification of the internal control in the same reaction mix where both processes are subject to the same concentrations of polymerase, nucleotide precursors, pH, salts and other additives.

Where an amplification method uses more than two primer binding sites to enable exponential amplification of a target polynucleic acid (for example Loop-mediated Isothermal Amplification (LAMP)), some of these primer sites are absolutely required for exponential amplification, whereby some merely affect the rate of amplification. As such, by varying which primer sites are present in the internal control, one can modulate amplification kinetics. This method forms one embodiment of the invention.

The generation of internal control polynucleotide sequences containing only a subset of desired primer binding sites and interspersed with sequences of choice is facile using modern recombinant DNA technologies. Further the generation of circular templates is known in the art via the use of DNA ligases.

In a further embodiment the internal control is amplified by different primers, or partially different primers, compared to the target polynucleotide sequence of interest so offering further means to amplify the internal control polynucleotide via a significantly different kinetic profile (FIG. 11). The word "different" thereby means that the primers used for amplification of the target polynucleic acid and the internal control have less than 80%, 75%, 70%, 65%, 60%, 55%, 50%, 45%, 40%, 35%, 30% or even less than 25% homology. Further, by limiting the amount of the primers used for amplification of the internal control, it is possible to limit the total amount of amplicon produced from the internal control polynucleic acid: this would mean that the signal from the internal control would be of lower amplitude than that of the test sample. "Limiting the amount" thereby means that the primers used for amplification of the internal control are added at concentrations which are less than 80%, 75%, 70%, 65%, 60%, 55%, 50%, 45%, 40%, 35%, 30%, 25%, 20%, 15%, 10% or even 5% than the concentrations of primers used for amplification of the target polynucleotide. It is only necessary that the mechanism of amplification afforded by these different primers is compatible with the amplification process associated with amplifying the test sample for the two processes to occur in the same vessel. The skilled person, armed with the teachings of the present invention, will be able to ascertain whether primers are suitable for use in the chosen amplification process.

In a further embodiment, an internal control is effected by taking advantage of the activity of certain proteins acting on polynucleotide sequences used as the internal control, whereby the protein generates priming sites for the polymerase used within the control polynucleotide, without the need for the binding of extraneous primers in the amplification process in such a way that de novo polynucleotides resulting from copying the supplied polynucleotide is generated at a linear (or slower) rate than that of polynucleotide of interest from the test-sample. As long as said protein can function under the amplification conditions then it is possible to combine both amplification reactions in the same vessel. Examples of such proteins include RNase Hs, Nickases, restriction endonucleases, & priming proteins (e.g. adenovirus priming protein pTP).

One way to achieve this (FIG. 12a) is to add to the reaction mixture a polynucleic acid (which is not similar to the sequence of the target polynucleic acid) which can be acted on by some additive to generate priming sites for nucleic acid synthesis. Preferably the additive is a protein that generates priming sites either via enzymatic action on the internal control polynucleotide or via some ability to act as a primer itself. For example, the inventors have found that TLi RNaseH can ellicit linear amplification of polynucleotides in a linear-like fashion under conditions used to perform methods such as Loop-mediated Isothermal Amplification (LAMP) or RDC. In this way an internal control can be achieved by adding to the amplification mixture the internal control polynucleotide (defined as a polynucleotide having no homology to the target polynucleotide and no deliberate primer binding sites for any of the primers used that can be acted on by the additive) and e.g. Tli RNaseH.

Alternatively, a further means to elicit amplification of an internal control without primer binding sites or additional reagents/proteins/enzymes, is to use as an internal control a polynucleic acid capable of self-replication under the amplification conditions used to amplify any target nucleic acid from the test sample (FIG. 12b). Examples of polynucleic acid sequences capable of self replication include circular templates capable of undergoing rolling circle amplification (as in linear RCA) or linear templates whereby hairpin structures generated at the 3' end cause the template to recopy it-self (this is an inherent feature of the LAMP technology for example). This forms a further embodiment of the invention.

Some nucleic acid amplification processes have been described as "linear" rather than "exponential" in the art, due to the fact that the kinetics of amplicon production appear to fit to a straight-line equation. In many cases, "linear" or "close to linear" kinetics have been sought to improve, for example, quantification methods or means to amplify various nucleic acid targets without biasing the amplicon to a particular population of sequences (something exponential amplification methods are more prone to do). Examples of "linear" or "close to linear" amplification methods include the aforementioned RCA (where only a single primer is used), asymmetric PCR (WO03040397) and also "Linear amplification of specific nucleic acid sequences" (U.S. Pat. No. 6,743,605), also the novel isothermal method described in WO/2007/030505, to name a few. In general, such "linear" methods describe amplifications processes whereby the target nucleic acid molecule is copied (perhaps repeatedly) but the copies are not themselves copied.

However, it is possible for an amplification processes to differ from another by virtue of the copies being only partially copied, or copied less efficiently or copied only under certain conditions.

In another embodiment of the present invention, different reaction kinetics are achieved by amplifying the first polynucleic acid and the internal control with the same or two similar amplification processes but in such a way that each amplification process can be independently controlled such as to affect the kinetics of amplification. The inventors have recognised that within a single vessel where the reagents for two distinct amplification processes are mixed, that one of the amplification processes can be favoured by virtue of the conditions chosen. In this way it is possible to affect the 'time to maximal amplification' as described in Richards' curve, in particular. This can allow kinetic differentiation of the two amplification processes and thus enable the present invention. Hence, in one embodiment amplification of the first polynucleic acid and the internal control is performed with the same amplification technique, wherein amplification of the first polynucleic acid and the internal control can be controlled by extrinsic conditions.

In one embodiment, the two amplification reactions are performed at different temperatures. In either amplification reactions where the temperature is repeatedly cycled or amplifications that are performed largely isothermally, the temperature thereby refers to the temperature at which the polynucleic acid is amplified and/or the temperature at which the primers bind to the primer binding sites on the polynucleic acid. In this embodiment it is possible to perform the amplification reaction at a temperature whereby one of the two amplification processes is favoured and hence occurs at a faster rate than the other amplification process then to later change the temperature such that the other amplification process is able to occur at a higher rate than before the temperature change. This could be achieved by careful selection of primers such that the melting temperature (Tm) of the primers associated with the respective processes were significantly different. Two primers are thereby considered to have a different Tm when the Tm of the primers differs by at least 1° C., 2° C., 3° C., 4° C., 5° C., 6° C., 7° C., 8° C., 9° C. or 10° C. A method wherein primers with different Tm values are used to amplify the first polynucleic acid and the internal control is an embodiment of the present invention.

Another way to achieve this, more applicable to PCR, is to choose two amplification processes whereby the extension time required for amplification is substantially different. The reaction may be started under conditions where one of the amplification reactions can occur given a particularly extension time but that the other is completely or substantially inhibited; following an appropriate period of time the extension time could, e.g. be increased to better suit the other amplification process. In this way it would be possible to ascertain whether amplification was observed (via a single signal type) from two separate amplification processes. Hence, a method wherein the amplification time is varied in order to achieve different reaction kinetics forms one embodiment of the invention.

An example of a means by which to produce amplification of an internal control of noticeably different kinetics to that used on the test-sample is shown in FIG. 5a. The BART-LAMP (Bioluminescent Assay in Real-Time-Loop-mediated Isothermal Amplification) technique which is used in this example is described in further detail below. Here is shown the BART output from the amplification of a target nucleic acid molecular where two of the six primers normally used in LAMP are omitted from the amplification mix. As a consequence, for a given amount of target DNA, the lag-time to reach maximal amplification is far longer than that for the full amplification mix containing all six primers. Further, the breadth of the BART light peak (a reflection of intrinsic amplification rate) is far broader than that normally observed with the full amplification mix containing all six primers. Therefore one means to implement the present invention is to have the internal control amplified via the LAMP method but omitting, for example, two of the six primers normally employed for amplification.

A further example of a means by which to produce amplification of an internal control of noticeably different kinetics to that used on the test-sample is shown in FIG. 5b. In this case, an amplification process which is dependent on Tli RNaseH and Bst Polymerase is shown acting on a DNA target consisting of DNA co-purified with Tli RHaseH during purification of Tli RNase H from recombinant $E.\ Coli$. The amplification produces very high molecular weight amplicon in a close-to linear fashion. As a result, the BART light peak appears very different (much broader) than light peaks resulting from, e.g. LAMP. As such, the type of amplification process demonstrated here exemplifies the present invention.

Verification that the Tli RNase H dependent amplification can act as an internal control is shown in FIG. 6. Here LAMP and the Tli RNase dependent amplification process are combined in the same tube. When the test is positive a sharp light peak from LAMP is seen at approximately 30 minutes, when the test is negative, the slow amplification from the Tli RNase dependent amplification process is observed instead. This reflects the model data shown in FIGS. 3a and 3b (remembering that BART reports the instantaneous rate of amplification whereas FIG. 3 shows the accumulation of nucleic acid). As such, it is possible to ascertain from a sample, whether or not the sample is positive, negative or inhibited by combining a LAMP reaction with the Tli RNase dependent amplification process.

Another important advantage of the present invention is that both amplification reactions can be detected with the same signal. Therefore, the method of the present invention obviates the need to purchase and maintain specialised equipment that would be necessary if more than one signal would need to be detected.

Various signals which can be used to detect polynucleic acid amplification are known in the art. These include electrochemical signals, turbidity, bioluminescent signals and fluorescent signals. Detection by the same signal thereby means that both amplification reactions are detected with the same kind of signal, for example bioluminescence.

In one embodiment the BART-LAMP reporter system is used to detect the signals. This system has been explained in detail in WO2004/062338 and WO2006/010948, which are hereby incorporated by reference. BART is an example of a reporter system designed for isothermal NAATs which gives a single type of signal from a sample: a bioluminescent signal. BART utilises the firefly luciferase-dependent detection of inorganic pyrophosphate: this is produced in large quantifies when 'target' sequences are detected using a NAAT. As such, molecular diagnostics can be achieved with BART simply by measuring the light emitted from closed tubes, in a homogeneous phase assay. BART is proven with several different NAATs, operating between 50-63° C. The BART reporter is a particularly effective means to follow the rate of amplification of a NAAT since the light output represents a measure of the instantaneous rate of amplification (whereas e.g. fluorescent outputs show the accumulation of a signal and hence the measurements have to be differentiated to obtain the amplification rates). By way of example, FIG. 4 shows BART being used in conjunction with LAMP to detect a dilution series of a particular target DNA molecule. Note that as the amount of target DNA in the sample decreases, the lag-phase to reach the time of maximal light increase (which is proportional to the lag-phase to reach maximal amplification) increases. Put differently, the time to reach the characteristic light peak associated with positive samples in BART increases in inverse proportion to the amount of target nucleic acid in the sample. It is stressed that whilst further examples make use of the BART reporter system, the present invention is not limited to the use of BART and is equally applicable to methods such as fluorescence, turbidity, other spectroscopic techniques or electrochemical measurement methods.

The second polynucleic acid, which acts as an internal control, needs to be chosen such that its sequence is sufficiently different from the sequence of the first polynucleotide. Two polynucleic acids are thereby deemed sufficiently different when they are less than 100%, 95%, 90%, 85%, 80%, 75%, 70%, 65%, 60%, 55%, 50%, 45%, 40%, 35%, 30%, 25%, 20%, 15%, 10%, or even 5% homologous. The amount of nucleic acid which needs to be added to the reaction will be evident to the person skilled in the art and can be easily determined, for example by testing various concentrations of the polynucleic acid in the NAAT which is to be used. However, it is expected that the amount of polynucleic acid which will need to be added lies between 10 µg and 100 ag, 100 ng and 100 fg or even 100 pg and 100 fg.

The term "internal control", as used herein, refers to any nucleic acid which is known to be amplified under certain conditions provided in the method of the invention. The internal control is thereby not restricted to polynucleic acids which were obtained from the same source as the test polynucleic acid, but rather encompasses any polynucleic acids given that such a polynucleic acid satisfies the criteria set out for the second polynucleic acid. The internal control may used as a control of the reaction itself and can also be used as a standard to quantitate the test-sample. Importantly, the inventors have shown that amplification of an internal control is inhibited by the presence of inhibitors in a sample, thereby confirming the suitability of the internal control as a control for amplification of the test sample (see FIG. 7).

Preferably, the method of the invention is performed in a sealed vessel. This is of great utility since it reduces or even prevents the possibility of the sample becoming contaminated. Moreover, it reduces or even prevents the possibility of the laboratory becoming contaminated. This is particularly important as if even one copy of the template nucleic acid were to escape into the laboratory, this could potentially contaminate other samples to be tested and give false-positive results. Thus, the ability to prevent contamination is of particular importance where a method of the invention is used in a diagnostic application. Methods by which to seal the reaction vessel will be evident to the person skilled in the art and include, but are not limited, to plastic films, wax, oil and foil covers.

A method according to the invention may be used in diagnostic applications. In particular the method allows identification of organisms in a patient sample and other samples. The organism may be any microorganisms, such as viruses, bacteria and fungi. The microorganism can be pathogenic but it may also be a non-pathogenic microorganism.

"Patient sample" refers to any sample taken from a patient and can include blood, stool, swabs, tissue samples, urine or spinal fluids. Other suitable patient samples and methods of extracting them are well known to those of skill in the art. A "patient" or "subject" from whom the sample is taken may be a human or a non-human animal. When a sample is not specifically referred to as a patient sample, the term also comprises samples taken from other sources. Examples include swabs from surfaces, water samples (for example waste water, marine water, lake water, drinking water), any other environmental samples (for example air) food samples, cosmetic products, pharmaceutical products, fermentation products, cell and microorganism cultures and other samples in which the detection of a microorganism is desirable.

In a further aspect, there is provided a kit for use in a method according to the invention. Preferably such a kit comprises all the components necessary to practise the method of the invention, except the target polynucleic acid which is to be tested, except where the target polynucleic acid forms part of a supplied positive control or in quantitative testing where the known amount of target is added for reference.

A kit for use in a method according to the invention preferably comprises a nucleic acid polymerase, the substrates for the nucleic acid polymerase and primers for amplification of the target polynucleic acid and the internal control. More preferably, the kit further comprises buffer reagents, such as a source of magnesium ions. Alternatively, a kit for use in a method according to the invention may comprise only some of these components and/or additional components. The sample and any other components that have been omitted from the kit may then be added to the kit during use.

When BART is used for detection of the polynucleic acids a thermostable luciferase, luciferin and an enzyme that converts PPi to ATP, such as ATP sulphurylase, and any other required substrates or cofactors of the enzyme that converts PPi to ATP, such as adenosine 5' phosphosulphate, may be included in the kit. Thus in one embodiment a kit for use with BART comprises nucleic acid polymerase, b) the internal standard, c) at least two primers suitable for amplification of the test-sample and the internal standard, d) a thermostable luciferase, e) luciferin, f) ATP sulphurylase, and g) adenosine 5' phosphosulphate.

Preferably, at least one of the components of the kit is lyophilised or is in another form which is suitable for storage in the kit. More preferably, all of the components of the kit are lyophilised or in one or more other forms suitable for storage. Such other forms include components to which stabilising factors have been added and/or a refrigerated or frozen mastermix that contains the components of the kit.

A further application of a method according to the invention is for determining whether a particular nucleic acid sequence is present in an organism's genetic code. For example, it could be used for determining whether the nucleic acid to which the template nucleic acid originates has been genetically modified, for detection of DNA associated with a particular non-genetically modified breed of plant or a genetically modified plant, for detection of DNA associated with pedigree breeds of animal or for medical or veterinary diagnostic applications such as genetic testing or forensic.

Various aspects and embodiments of the present invention will now be described in more detail by way of example. It will be appreciated that modification of detail may be made without departing from the scope of the invention.

EXAMPLES

Example 1

Figure 1B:
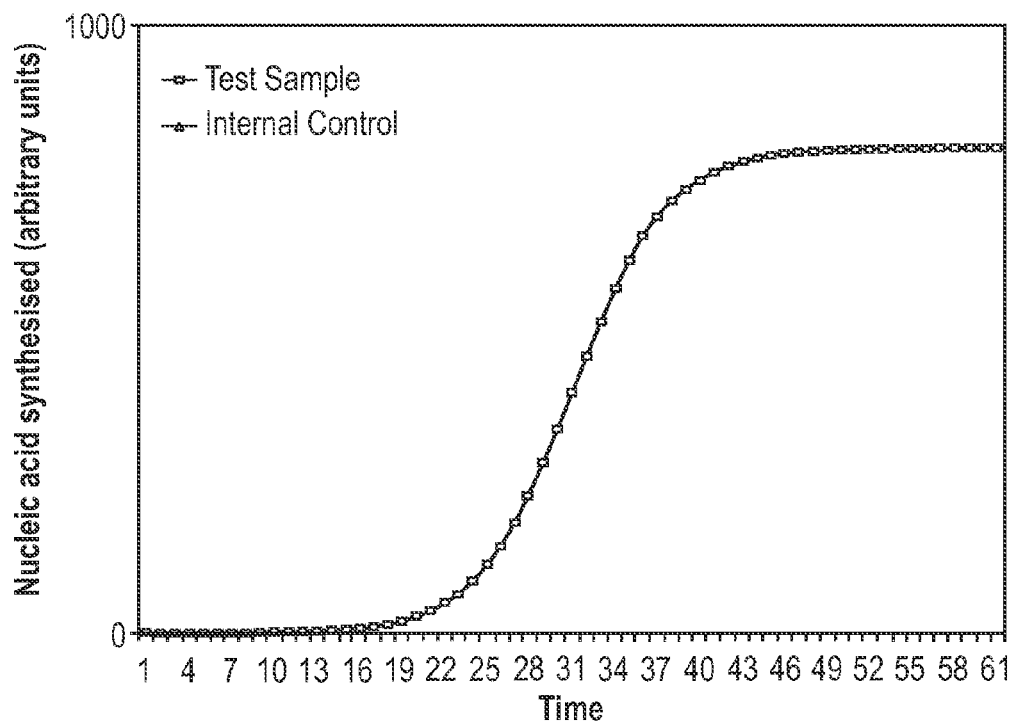
FIG. 1. Example of a mathematical model for a growth/amplification curve known as Richards' Curve. a) version of the Richards' curve equation adapted for nucleic acid amplification; b) two amplification processes with identical kinetics c) two amplification processes which differ in the amount of amplicon they can finally produce d) two amplification processes which differ in the time it takes to reach maximal amplification e) two amplification processes with differing amplification rates f) two amplification processes where, at the time to reach maximal amplification, the signal differs between how close they are to the respective asymptotes g) two amplification processes which are both described by Richards' curve: N.B. one of the processes appears at first inspection to be linear (i.e. a straight line). As such, in practice, it is not always easy (or necessary) to be sure whether a process is truly exponential or linear from a particular set of measurements; the issue with respect to the present invention is whether the separate processes can be unambiguously deconvoluted from the shared signal.
Figure 1C:
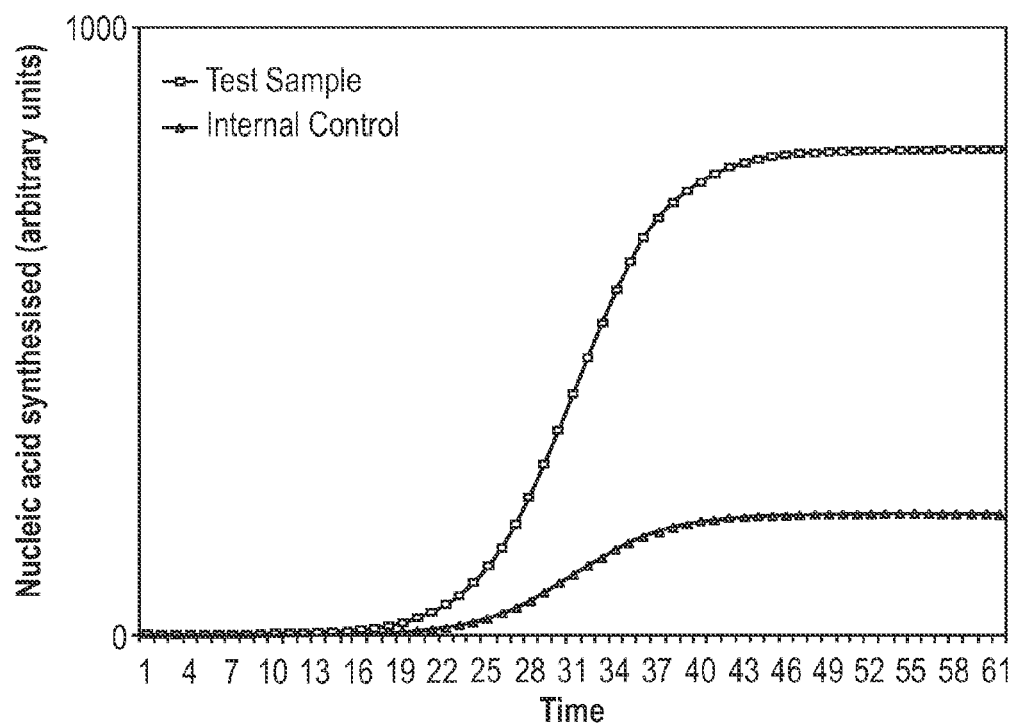
Figure 1D:
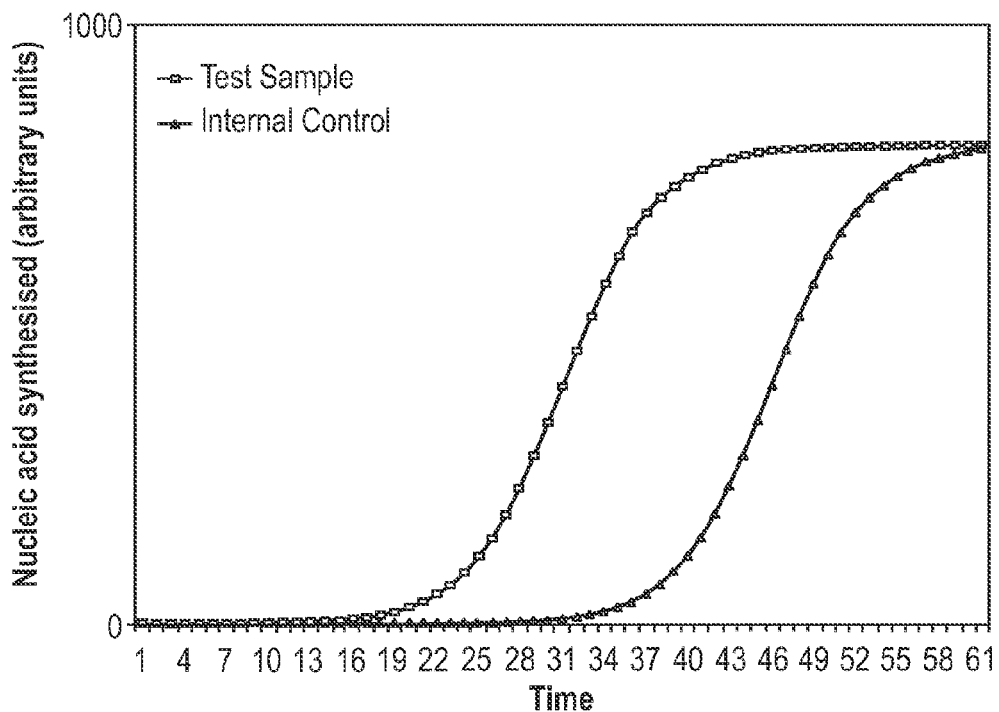
Figure 1E:
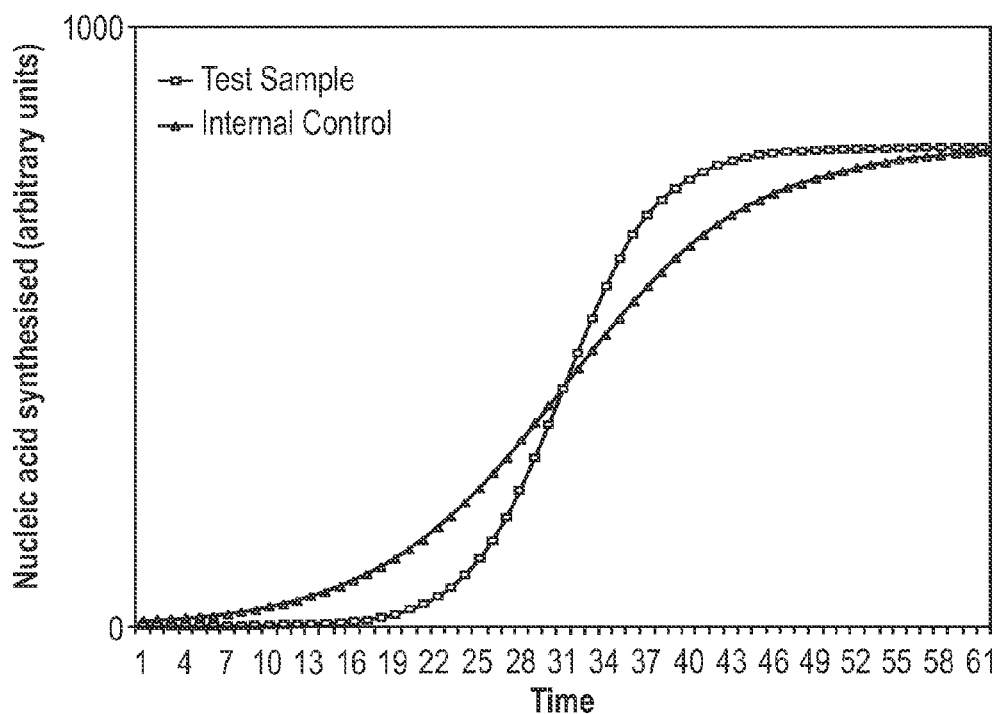
Figure 1F:
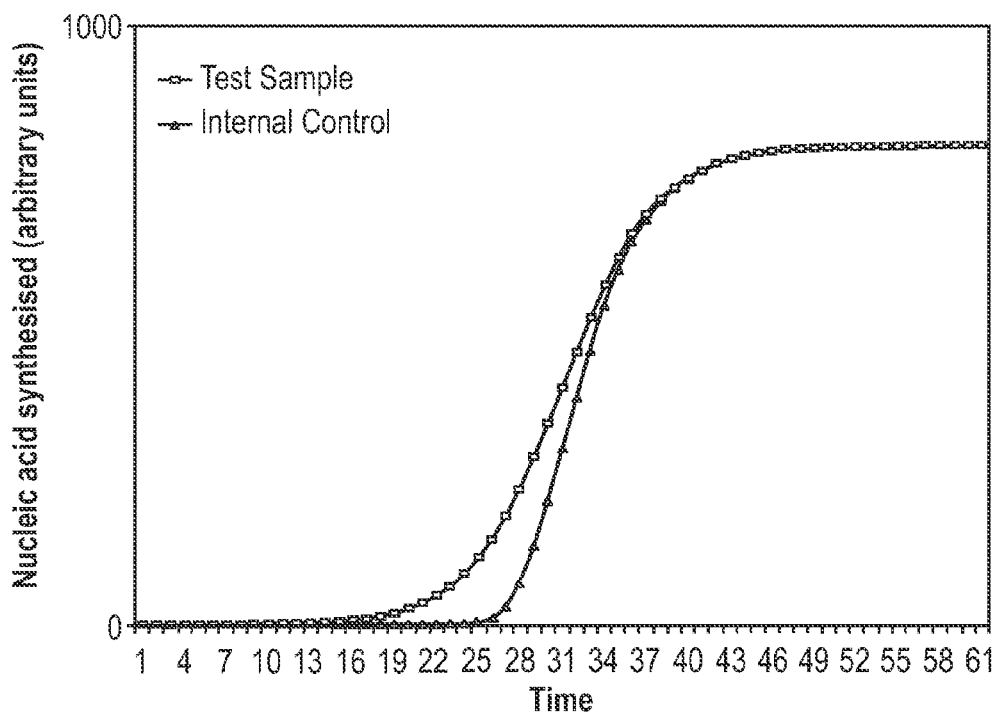
Figure 1G:
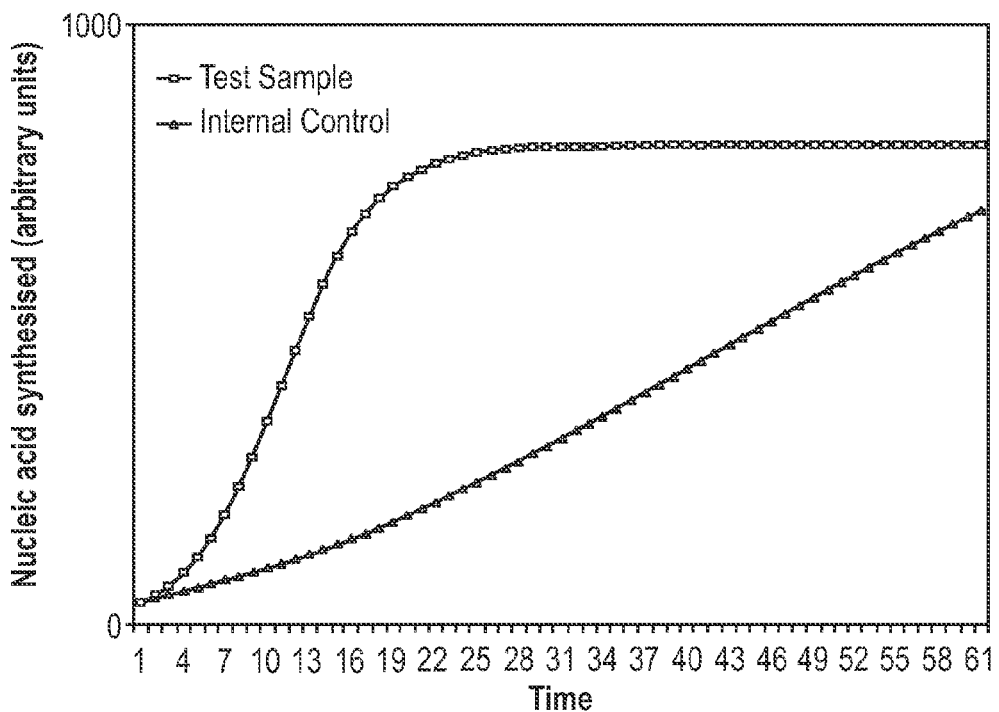
Figure 2C:
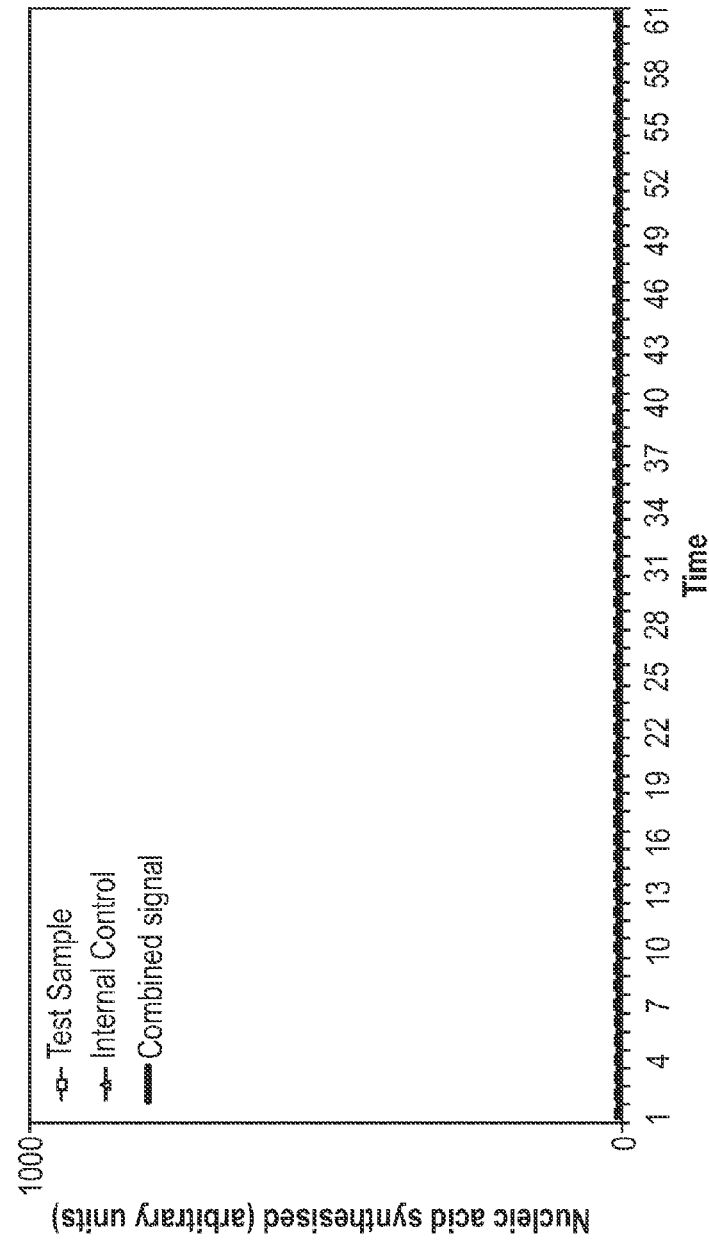
FIG. 2. Mathematical model of the invention. This demonstrates the general principle that it is possible to follow two separate processes, in a closed tube, using a single signal so long as the two processes give signal outputs that are sufficiently different by way of their kinetic description or amplitude.
Figure 3B:
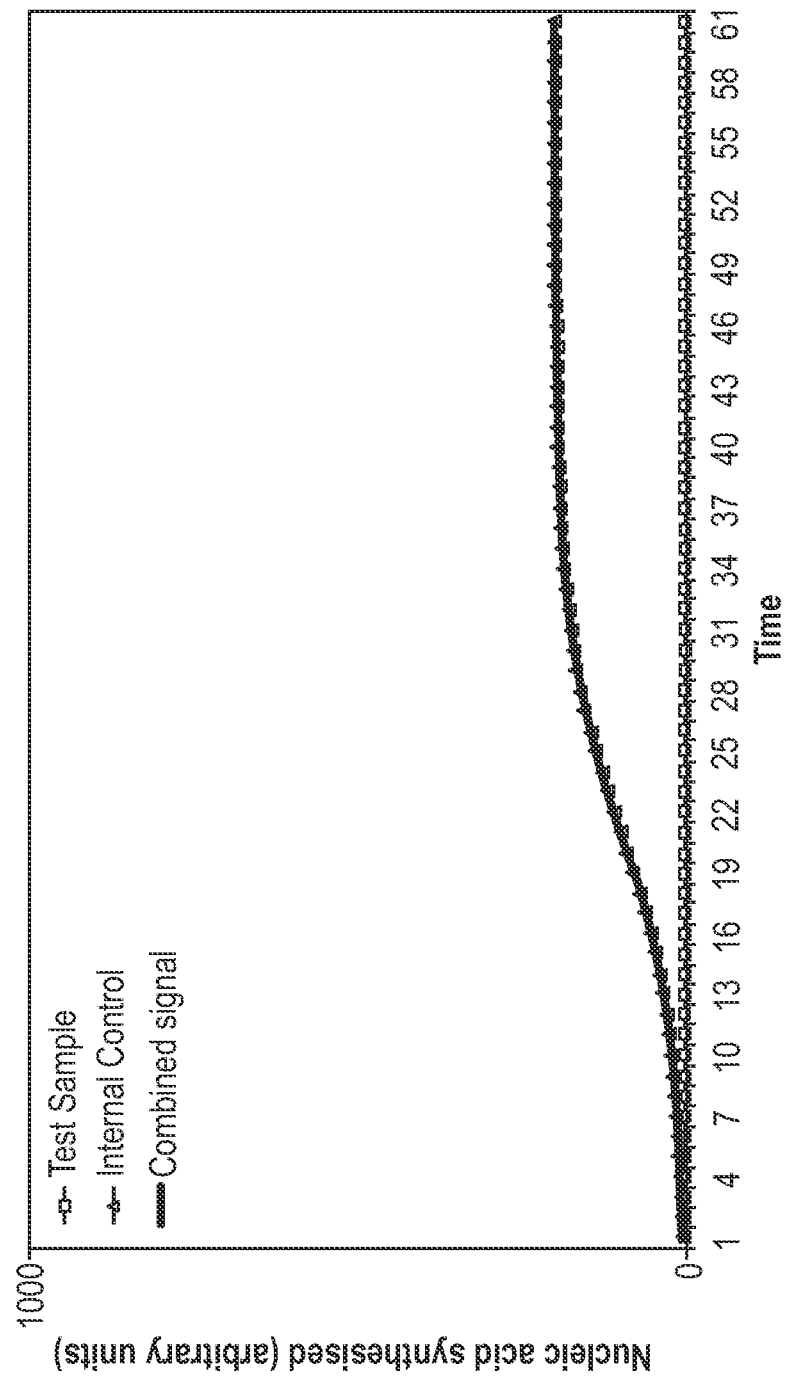
FIG. 3. Mathematical model of the invention demonstrating that, even when the two processes are occurring simultaneously, as opposed to sequentially, as shown in FIG. 1, it remains possible to differentiate amplification from the test sample compared to amplification from the control by virtue of differences in the intrinsic rate of amplification.
Figure 4:
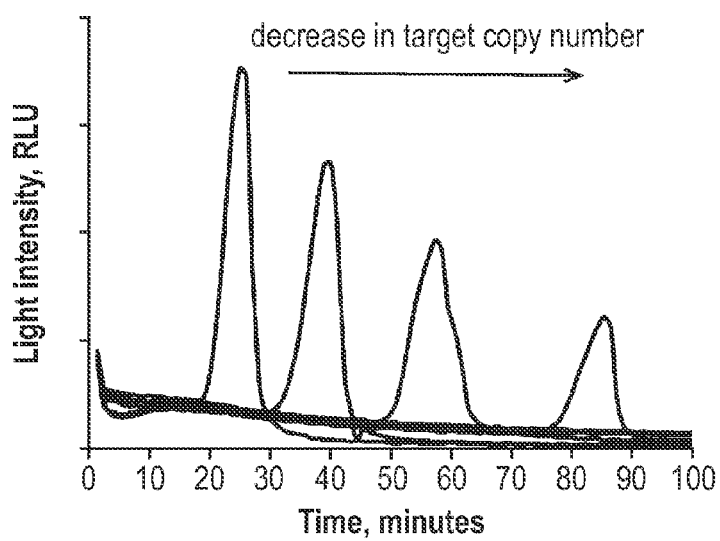
FIG. 4. Exponential amplification of a dilution series of a target nucleic acid sequence using the LAMP amplification technology in combination with the BART reporter technology. The BART technology is a bioluminescent reporter system whereby only a single type of signal can be emitted from the sample. BART, unlike other reporter systems, gives both an increase and rapid decrease during amplification: the time to the peak of light is inversely proportional to the amount of target nucleic acid in the sample. Further, the width of the peak of light is a function of the inherent rate of amplification of the NAAT being monitored.

LAMP-BART of genomic *Salmonella* DNA purified by ChargeSwitch® direct gDNA Kit (Invitrogen) was amplified in Lamp-BART at 55° C. on Lucy, bespoke imaging hardware (Lumora). The reaction mixture contained: 0.8 µM LampB primer (AACCTTGTGGAGCATATTCGTGGTTTTC-CGCCATTGGCGAATTTATG), 0.8 µM LampF primer (TCTCTTGGCGC-CCACAATGTTTTAAGCGAACGTGTTTCCG), 0.4 µM LoopB primer (CAATGGCGCGTTATATTTG), 0.4 µM LoopF primer (GAGCGCTTCCAT-AATTAATTTC), 0.2 µM DisplB primer (CATTACTGCTCGTAATTC), 0.2 µM DisplF primer (ATATCTGAAGTTTTGCAGC) (MWG), 1.6 mM dNTPs (total) (Invitrogen), 0.16 U/µl Bst (NEW ENGLAND BIOLABS), 0.1 mg/ml luciferin (Europa Bioproducts), 0.5 mM adenosine 5'-phosphosulphate (Biolog), 5.6 µg/µl firefly luciferase (Ultra Glow, Promega), 0.125 U/ml ATP-sulphurylase (Sigma) in 1× Thermopol buffer (New England Biolabs) with some stabilisers and additives. The total volume of each reaction was 20 µl. Observed BART signals responded to the exponential DNA amplification by an increase in light followed by a prompt decrease in light for positive samples containing different starting target copy number and by a steady gradual decay for negative sample that did not contain any target DNA (FIG. 4).

Example 2

Figure 5A:
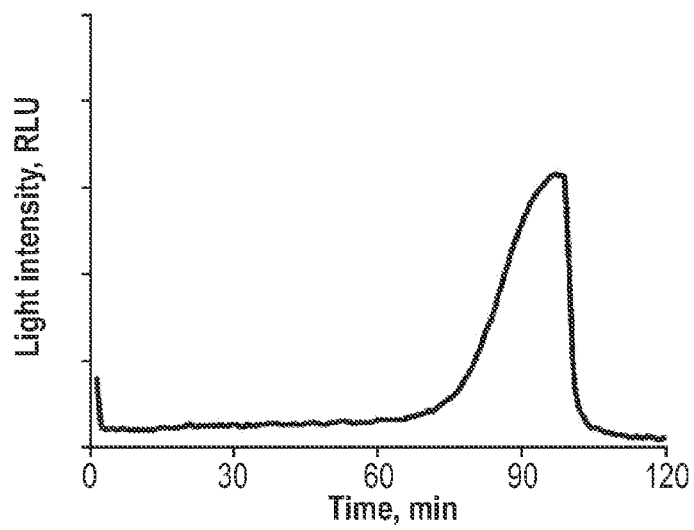
FIG. 5*a*. Delayed exponential amplification of a target nucleic acid.

Delayed exponential amplification of a target nucleic acid was observed under the conditions identical to those in Example 1 but omitting LoopB and LoopF primers. The lag-time preceding the flash signal was detected even for high copy number of target nucleic acid and became significantly longer; the exponential rise was much slower (FIG. 5a). The half-width of the flash observed in this example was three times bigger than in the exponential amplification described in Example 1.

Figure 5B:
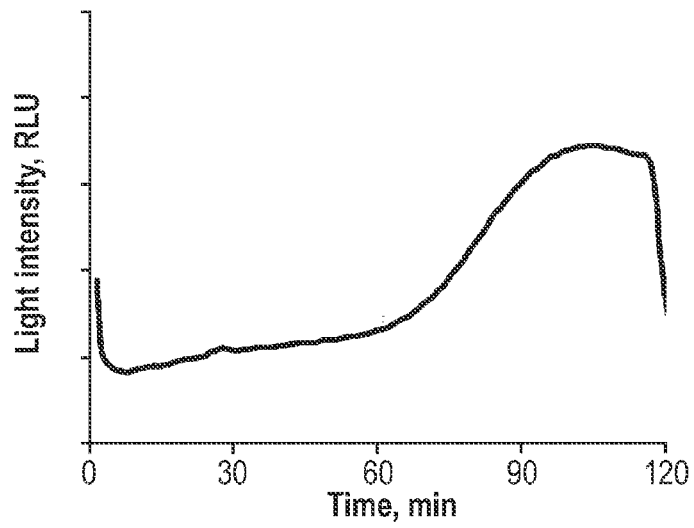
FIG. 5*b*. Reduced rate of change of bioluminescent output observed in isothermal amplification of nucleic acids via a Tli-RNaseH dependent process that shows a much slower inherent rate of amplification than compared to e.g. LAMP. In fact the process appears to be close to a linear rate of amplification. The precise mechanism of this Tli-RNaseH dependent process is unclear but appears to be caused by the action of Tli-RNaseH on DNA containing small amounts of RNA-DNA heteroduplexes originating from either or both transcription or DNA Primase.

Reduced rate of amplification was demonstrated by a non-specific, linear-like isothermal amplification of nucleic acids via a Tli-RNaseH driven process at 55° C. on Lucy, bespoke imaging hardware (Lumora). The reaction mixture contained: 0.32 U/µl Tli-RNaseH (Takara), 1.6 mM dNTPs (total) (Invitrogen), 0.16 U/µl Bst (New England Biolabs), 0.1 mg/ml luciferin (Europa Bioproducts), 0.5 mM adenosine 5'-phosphosulphate (Biolog), 5.6 µg/µl firefly luciferase (Ultra Glow, Promega), 0.125 U/ml ATP-sulphurylase (Sigma) in 1× Thermopol buffer (New England Biolabs) with some stabilisers and additives, DNA target for the Tli-RNaseH driven process. The total volume of each reaction was 20 µl. Observed BART signals responded to the nucleic acid amplification in a significantly slowed down, almost linear, gradual rise followed by a decrease in light output (FIG. 5b). The half-width of these signals was even bigger than in the previous case.

Example 3

Figure 6:
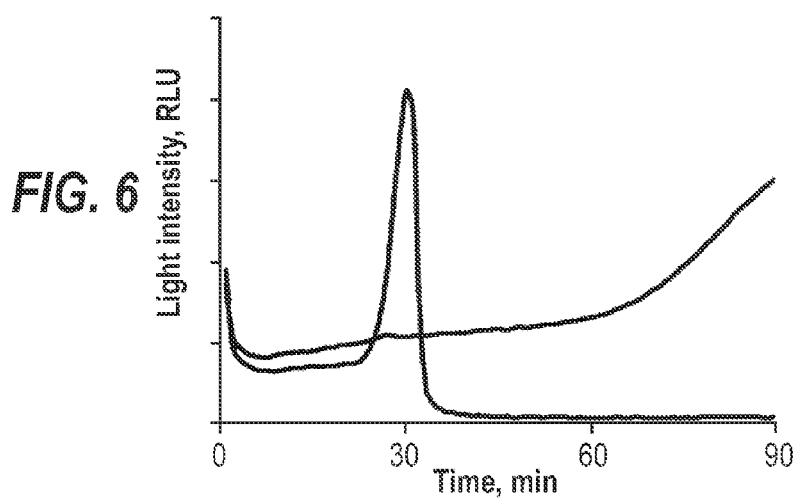
FIG. 6. Exponential and non-exponential amplification recorded from a single-tube assay in the presence (1) or absence (2) of target nucleic acid.

Exponential amplification of genomic *Salmonella* DNA by LAMP was combined in a single tube assay with the aforementioned near-linear Tli-RNaseH dependent amplification of nucleic acids and monitored by BART at 55° C. on Lucy, bespoke imaging hardware (Lumora). The reaction mixture contained: 0.8 µM LampB primer, 0.8 µM LampF primer, 0.4 µM LoopB primer, 0.4 µM LoopF primer, 0.2 µM DisplB primer, 0.2 µM DisplF primer (MWG), 0.32 U/µl Tli-RNaseH (Takara), 1.6 mM dNTPs (total) (Invitrogen), 0.16 U/µl Bst (New England Biolabs), 0.1 mg/ml luciferin (Europa Bioproducts), 0.5 mM adenosine 5'-phosphosulphate (Biolog), 5.6 µg/µl firefly luciferase (Ultra Glow, Promega), 0.125 U/ml ATP-sulphurylase (Sigma) in 1× Thermopol buffer (New England Biolabs) with some stabilisers and additives, DNA target for Tli-RNaseH driven amplification. Total volume of each reaction was 20 Sample containing target sequence responded with a sharp flash reflecting fast exponential production of DNA. Sample without the target sequence but with the DNA target for Tli-RNaseH driven amplification responded (i.e. the internal control) with a slow rise of the light signal (FIG. 6)

Example 4

Figure 7A:
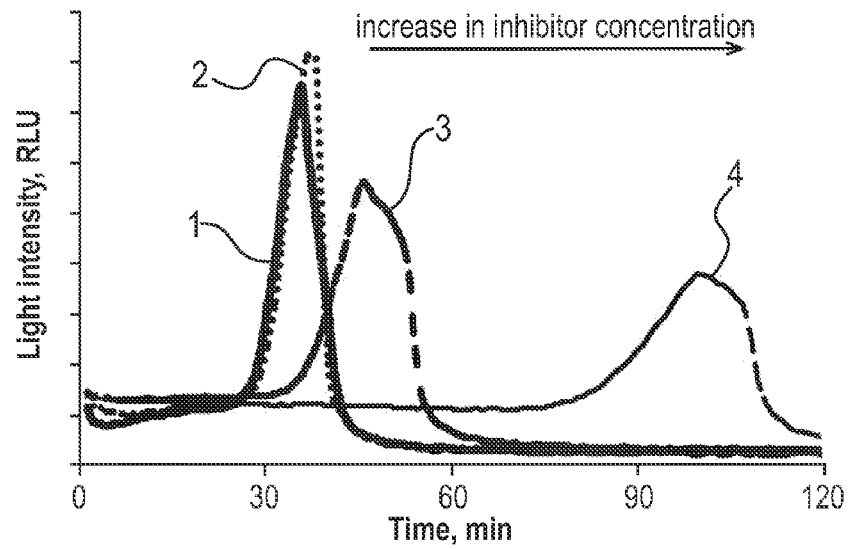
FIG. 7. Inhibition of genomic DNA amplification in Lamp-BART with different concentrations of Buffered Peptone Water (BPW), a known inhibitor of NAATs, or CTP. 7a. Inhibition of target-containing sample (1—no BPW, 2—5× diluted BPW, 3—2× diluted, 4—non-diluted BPW); 7b. Inhibition of no-template control (1—no BPW, 2—5× diluted BPW, 3—2× diluted, 4—non-diluted BPW); 7c. Inhibition of target-containing sample (1-3) and no-template control with different concentrations of CTP (1 and 4—no CTP, 2 and 5—2 mM CTP, 3 and 6—3 mM CTP).
Figure 7B:
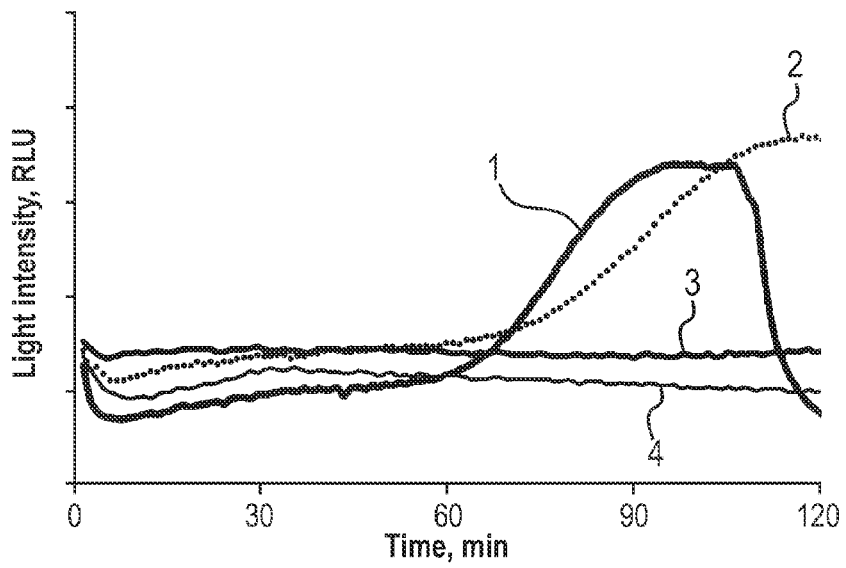
Figure 7C:
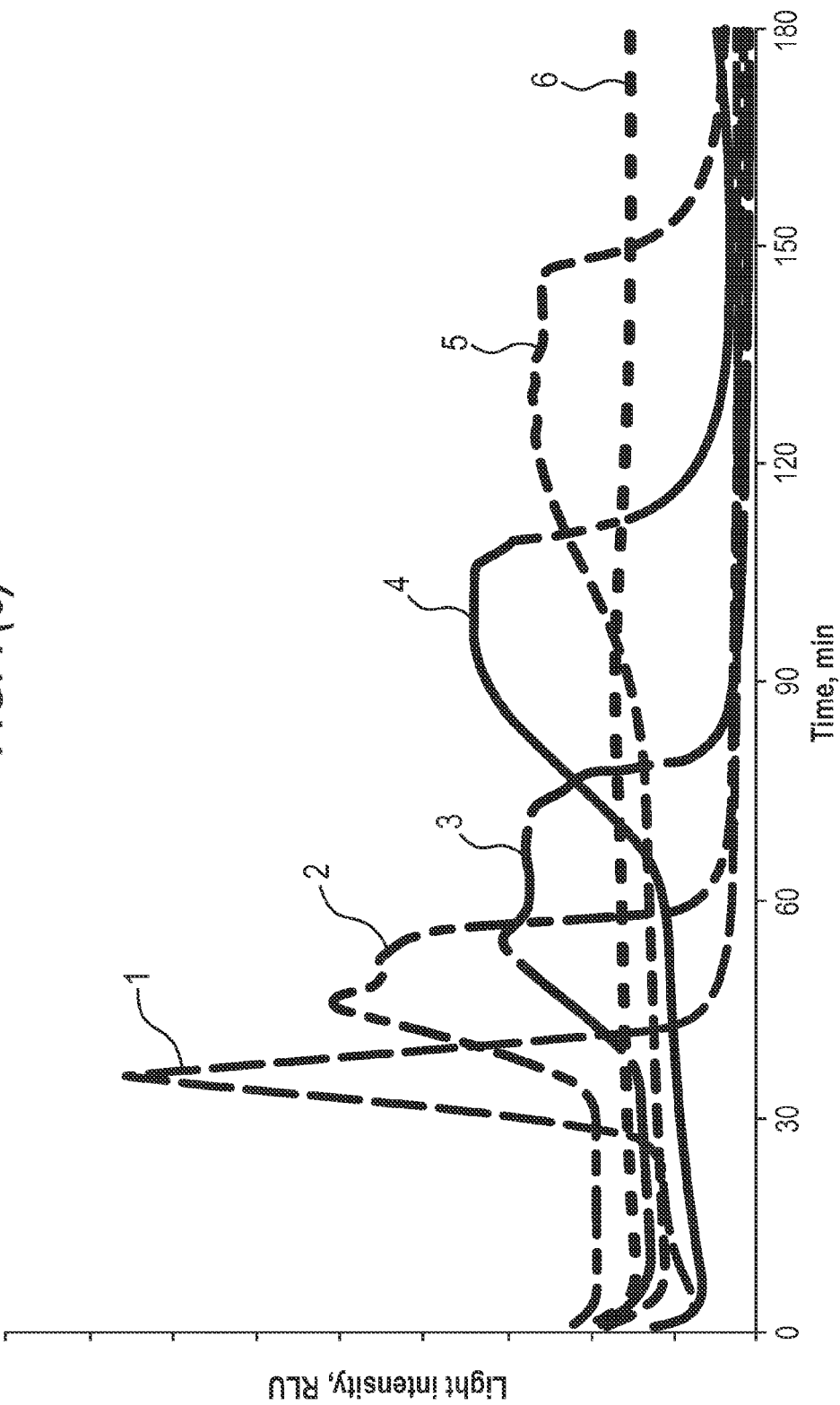

Inhibition of amplification of genomic DNA from *Salmonella* (2 ng per assay) with buffered peptone water (BPW) or CTP was demonstrated in LAMP-BART under the conditions described in Example 3. 5 µl of BPW or CTP pre-diluted to different concentrations was added into 15 µl of the assay mixture either containing target DNA, positive samples, or no-target DNA negative samples. The results observed in positive and negative samples with BPW are shown in FIG. 7a and FIG. 7b and with CTP in FIG. 7c, respectively. Addition of non-diluted and 2× pre-diluted BPW completely inhibited non-exponential amplification in negative samples and significantly slowed down exponential amplification in positive samples. 5× diluted BPW had only a slight slowing down effect on both amplifications. Similarly addition of 3 mM CTP completely inhibited non-exponential amplification in negative samples and slowed down significantly exponential amplification in positive sample, while 2 mM CTP just slowed down both amplifications. This shows that the near-linear, Tli-RNaseH driven amplification acted as an effective internal control for the detection of inhibitors.

Example 5

Figure 8A:
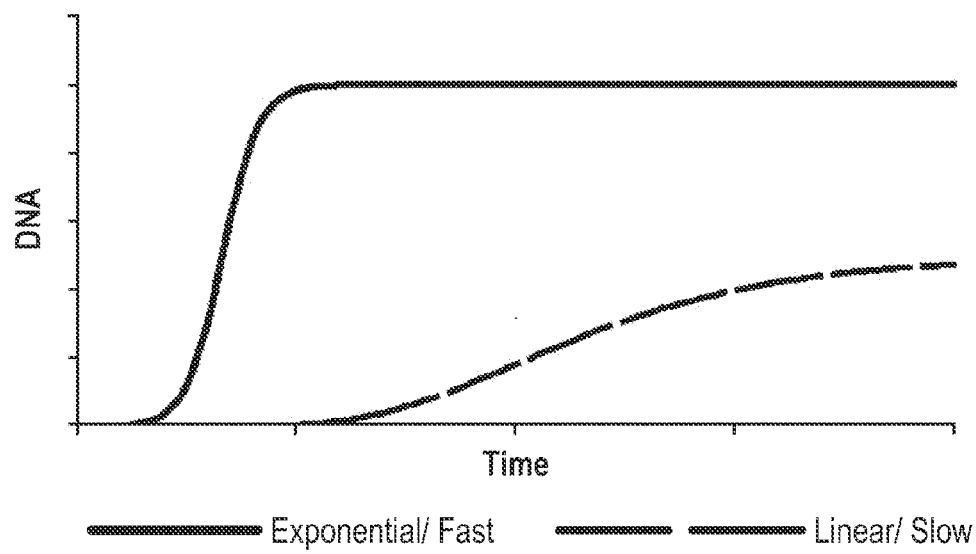
FIG. 8. Mathematical model of the invention demonstrating two processes occurring simultaneously in the absence and presence of inhibitors. a) Two types of kinetics in the absence of inhibitors; b) Real-time monitoring of positive and negative samples with internal inhibition control.
Figure 8B:
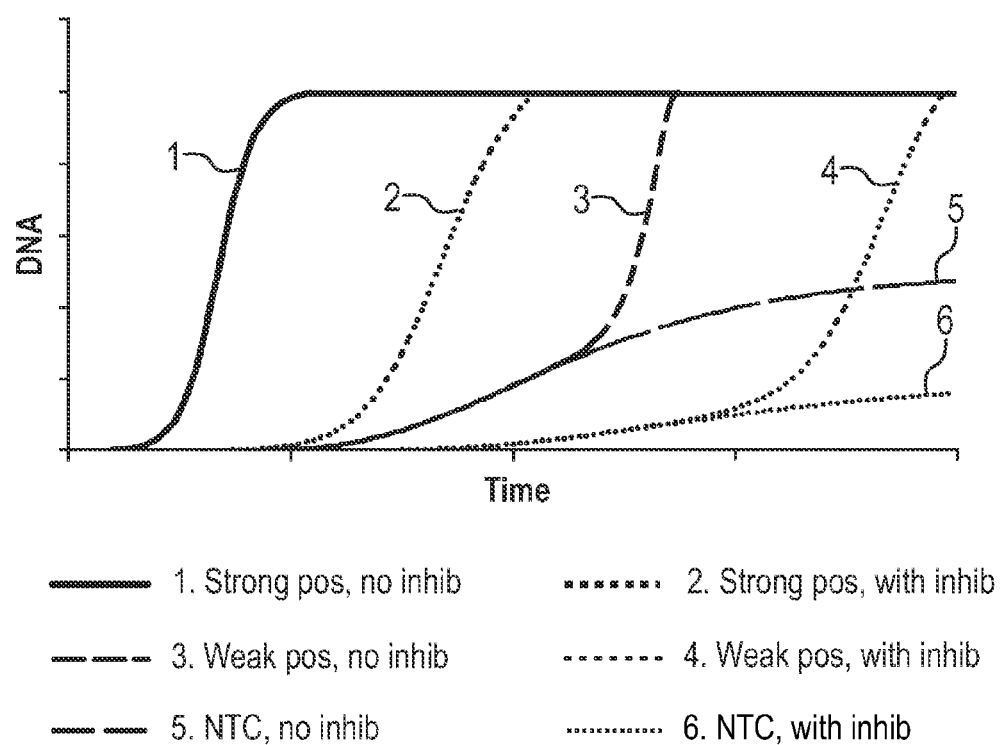
Figure 9:
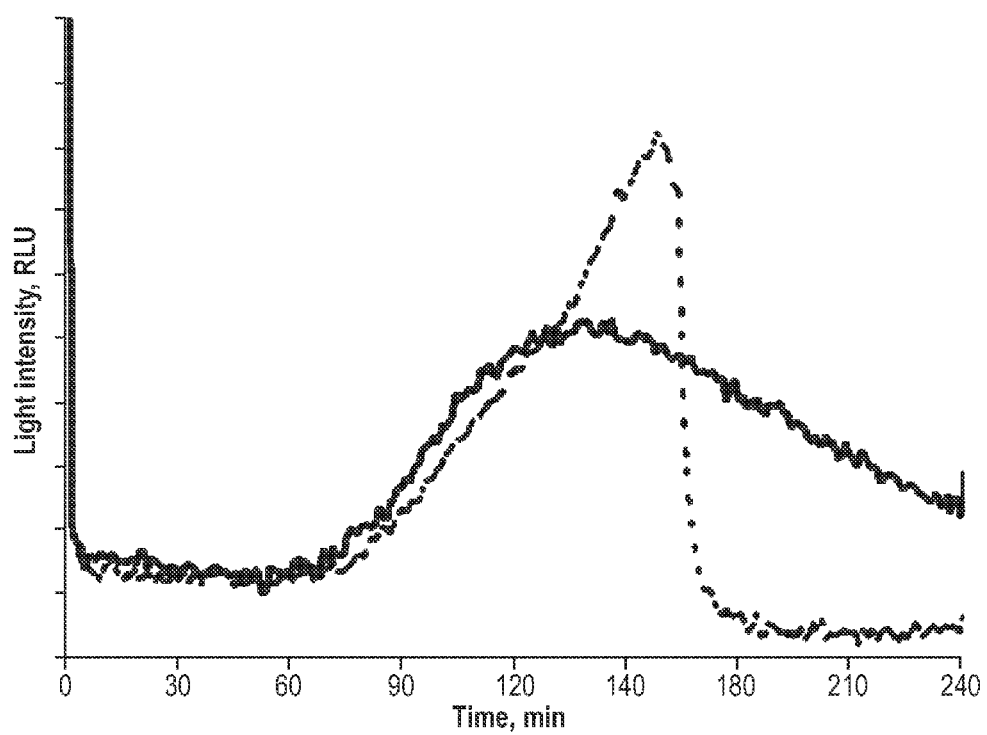
FIG. 9. Amplification of a target DNA molecule, via the NAAT known as RDC, in the presence of an internal control based on RNaseH Tli-based amplification as followed by BART. In dotted light grey is shown the successful amplification of the target DNA molecule as evidenced by the rapid increase and then more rapid still decrease in light from the sample. This amplification takes place in the presence of the internal control. In solid black is shown the result of amplification when no target DNA is present and the only amplification detected is from the internal control. In this case, the light peak from the BART reporter system is visibly broader than that of the target DNA molecule, in particular, it lacks the rapid decrease in light after maximal light emissions, associated with exponential amplification processes. As such, in regarding the black trace, it is facile for an observer to establish that a) the amplification reagents are not inhibited, since amplification has occurred, but that b) amplification is from the internal control and not the test-sample as the shape of the BART output is not that associated with rapid exponential amplification. A computer algorithm would be able to distinguish between the two curves on the basis that the positive result has a far faster negative rate of change following the light peak compared to the internal control.
Figure 10:
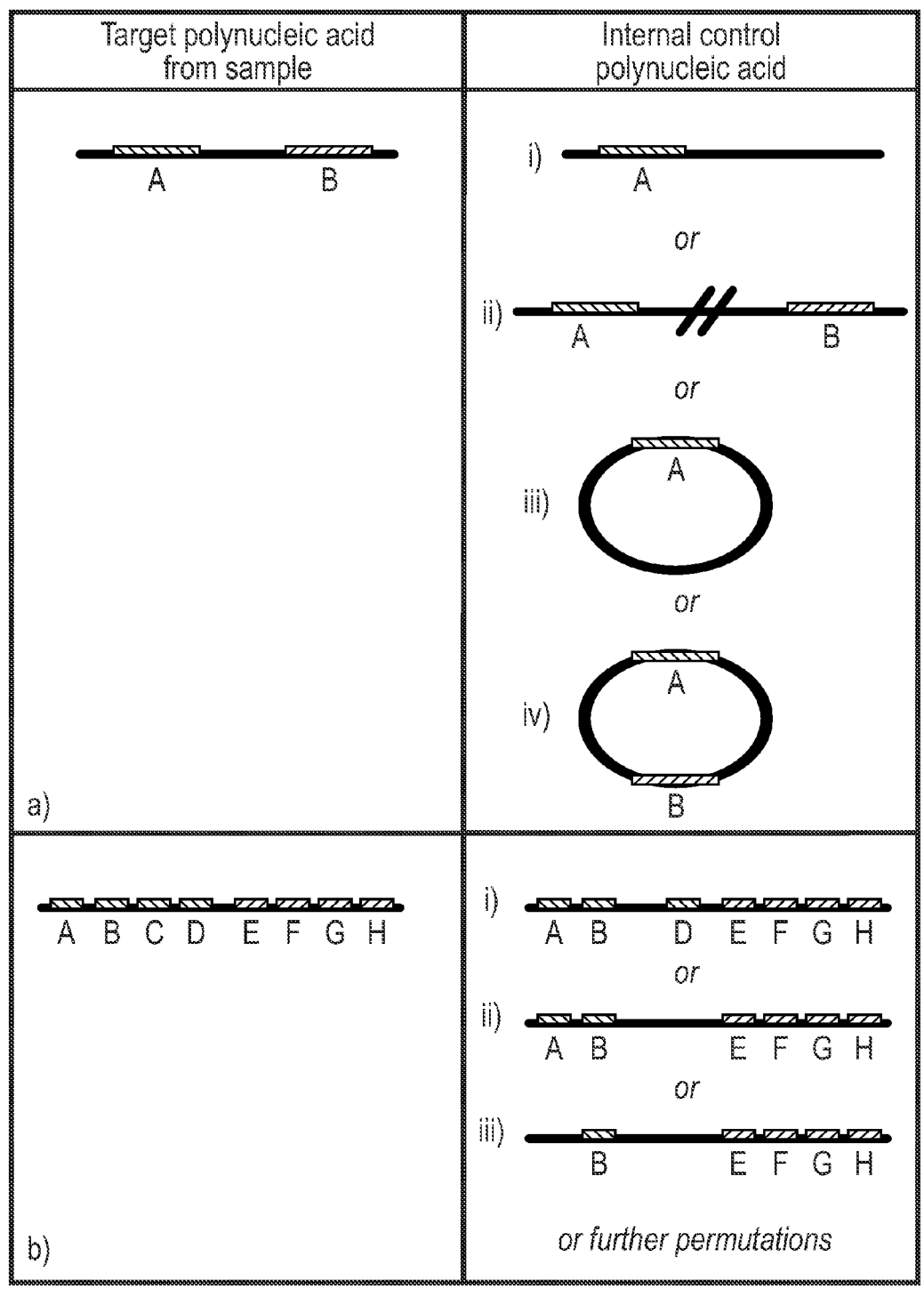
FIG. 10 shows a variety of methods to achieve, in a single vessel, two amplification processes of different kinetics.
Figure 11:
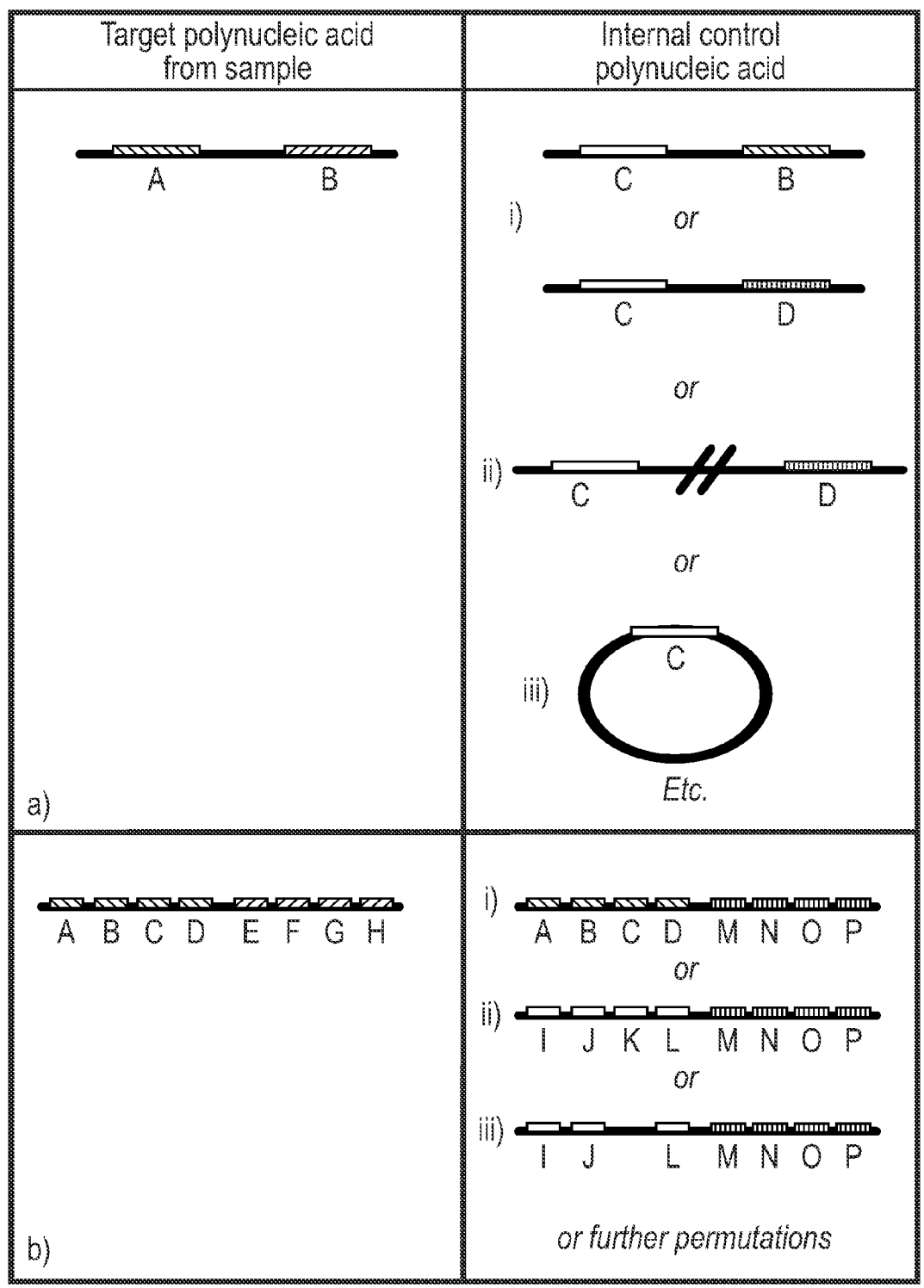
FIG. 11 reflects all the features shown in FIG. 10 except in this case the internal control polynucleotide may contain primer binding sites for primers not used to amplify the target polynucleic acid.
Figure 12:
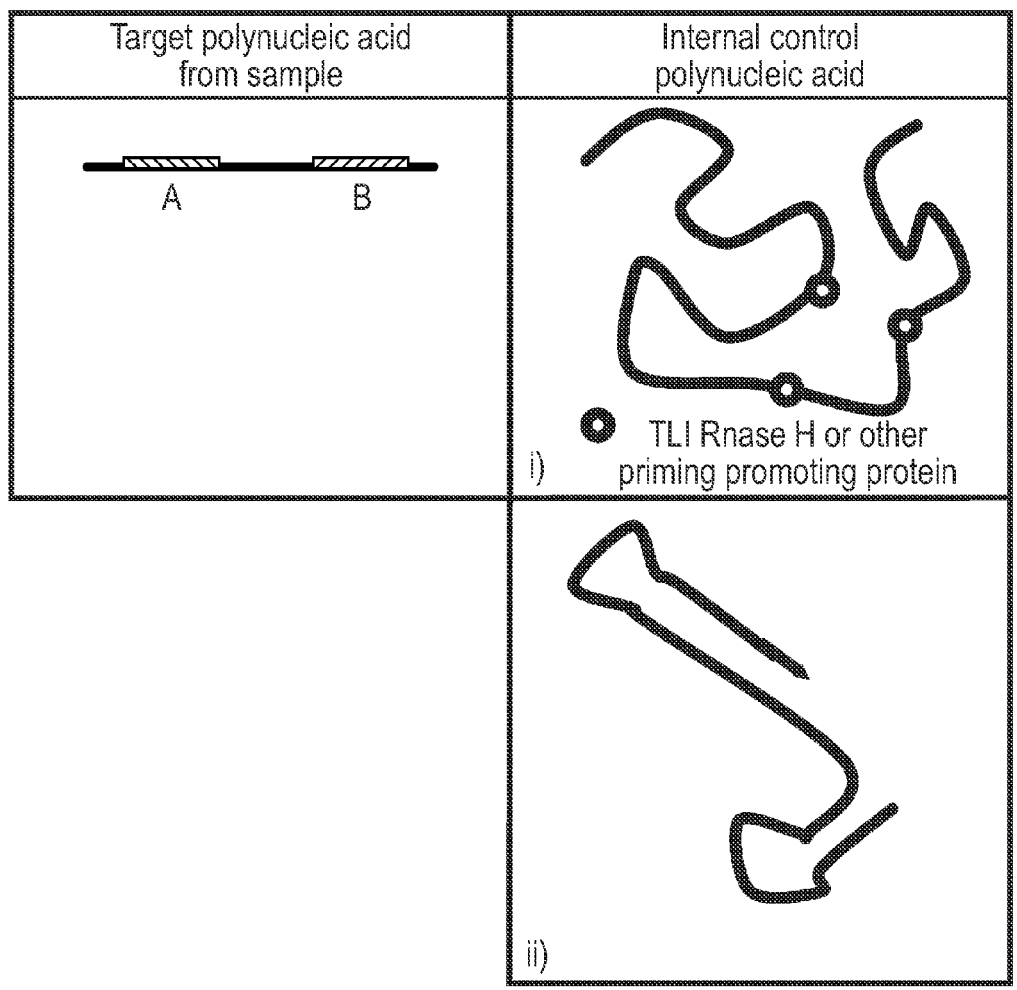
FIG. 12 shows two alternatives to using internal control polynucleotides which have primer binding sites either for the primers used to amplify the target polynucleic acid or any further primers to help amplify the internal control.

The results of mathematic modelling of exponential and slow non-exponential kinetics required for internal inhibition control in NAAT in a single-tube assay are shown in FIG. 8a. The results of mathematic modelling of the effect of inhibitor on the single parameter in real-time detection of NAAT with an internal inhibition control are shown in FIG. 8b.

Example 6

A reaction mixture of the following constituents was made up at 4° C.: 20 mM Tris-HCl pH 8.8, 10 mM $(NH_4)_2SO_4$, 10 mM KCl, 4.8 mM $MgSO_4$, 0.1% Triton X-100, 500 µM of each dNTP, 10 U RNaseOut, 25 pmol Lm-InlA-RDCus3r2d (tgactgaaccagctaagcctgUAAaa), 25 pmol Lm-InlA-RDCus3r2d (cgttgctgtgtagctgttaatacUAAat), 6.25 pmol InlA Df-v2 (ataatctactgtttgagatg), 6.25 pmol InlA Db-v2 (taatgctaagtttcatgtg), 0.1 mg/ml LH2, 0.5 mM APS, 140 µg rLUC, 3.125 U ATP sulphurylase, 4 U Bst polymerase large fragment, 1 U Tli RNase H II. 20 µl of the above mixture was added to two separate tubes containing 5 µl of either 10 or 0 copies of a plasmid harbouring the InlA gene. The reactions were placed from 4° C. to a BART imaging system and ran for 260 minutes at 60° C. with 240 image acquisitions. In dotted light grey is shown the successful amplification of the target DNA molecule as evidenced by the rapid increase and then more rapid still decrease in light from the sample. This amplification takes place in the presence of the internal control. In solid black is shown the result of amplification when no target DNA is present and the only amplification detected is from the internal control.

The invention claimed is:

1. A method for determining the presence and/or amount of a first polynucleic acid in a sample comprising subjecting the sample to nucleic acid amplification in which the presence and/or amount of the first nucleic acid is detectable by the presence of a reporter signal generated by polynucleic acid formation from the amplification of the first polynucleic acid, wherein the method comprises nucleic acid amplification of the first polynucleic acid and a second polynucleic acid in the same reaction vessel, the nucleic acid amplification being performed with a predetermined amount of the second polynucleic acid, wherein the product of the amplification of the first polynucleic acid and the product of the amplification of the second polynucleic acid are detected by the same reporter signal and wherein the reporter signals from amplification of the first polynucleic acid and the second polynucleic acid are resolved based on a set of readings of signal against time, the product of the second polynucleic acid amplification being produced with different reaction kinetics from the product of the amplification of the first polynucleic acid such that the second polynucleic acid acts as an internal control for the method.

2. The method of claim 1 wherein the first polynucleic acid is amplified using exponential nucleic acid amplification and the second polynucleic acid is amplified using non-exponential nucleic amplification.

3. The method of claim 2, wherein the nucleic acid amplification involves the use of one or more primers binding to primer binding sites on the polynucleic acid and at least one of the primer binding sites used to exponentially amplify the first polynucleic acid is either partially absent or non-optimal in the second polynucleic acid in order to achieve different reaction kinetics.

4. The method of claim 3, wherein one of the primer binding sites present on the first polynucleic acid is absent on the second polynucleic acid and wherein the nucleic acid amplification requires two primer binding sites.

5. The method of claim 3, wherein one or more primer binding sites are present on a circular polynucleic acid molecule but in an orientation that prevents exponential amplification and wherein the amplification reaction requires two primer binding sites.

6. The method of claim 1 wherein the first polynucleic acid is amplified using non-exponential nucleic acid amplification and the second polynucleic acid is amplified using exponential nucleic acid amplification.

7. The method of claim 2 or 6, wherein the exponential nucleic acid amplification is selected from the group consisting of polymerase chain reaction, Strand Displacement Amplification (SDA), Loop-mediated Isothermal Amplification (LAMP), Isothermal Chimeric Amplification of Nucleic Acids (ICAN), SMart Amplification Process (SMAP), Chimeric Displacement Reaction (RDC), (exponential)-rolling circle amplification (exponential-RCA), Nucleic Acid Sequence Based Amplification (NASBA), Transcription Mediated Amplification (TMA), Helicase Dependent Amplification (HAD) and Recombinase polymerase amplification (RPA).

8. The method of claim 2 or 6, wherein the non-exponential nucleic acid amplification is linear nucleic amplification is selected from the group consisting of rolling circle amplification, asymmetric polymerase chain reaction (asymmetric PCR), Rolling circle amplification, asymmetric PCR and asymmetric LAMP.

9. The method of claim 1 wherein the first polynucleic acid is amplified using exponential nucleic acid amplification and the second polynucleic acid is amplified using exponential nucleic acid amplification, and wherein the two nucleic acid amplifications have different reaction kinetics.

10. The method of claim 9, wherein the nucleic acid amplification of the first polynucleic acid and the second polynucleic acid differ in one or more of the following parameters:
  a) amplitude
  b) lag-time before maximal amplification or
  c) intrinsic rate of amplification 11. The method of claim 9, wherein the nucleic acid amplification involves the use of primers binding to two primer binding sites on the polynucleic acid and wherein the primer binding sites are more separated on the second polynucleic acid compared to the first polynucleic acid.

12. The method of claim 9, wherein the nucleic acid amplification involves the use of primers binding to two primer binding sites on the second polynucleic acid and wherein the primer binding sites are separated by a region which is slower for a polymerase to copy compared to the first polynucleic acid.

13. The method of claim 9, wherein the nucleic acid amplification involves the use of primers binding to two primer binding sites on the polynucleic acid and wherein one or both of the primer sites on the second polynucleic acid contain mismatches that cause amplification to occur less efficiently in the second polynucleic acid compared to amplification of the first polynucleic acid.

14. The method of claim 1, wherein the first polynucleic acid and the second polynucleic acid are amplified by different nucleic acid amplification techniques.

15. The method of claim 1, wherein the first polynucleic acid and the second polynucleic acid have less than 100% homology.

16. The method of claim 1, wherein the reaction is performed in a sealed vessel.

17. The method of claim 1, wherein the signal used for detection of the amplification products is selected from the group consisting of: a fluorescent signal, an electrochemical signal, a bioluminescent signal and turbidity.

18. The method of claim 17, wherein the bioluminescent signal is detected by a real time bioluminescent assay.

19. The method of claim 1, wherein amplification of the first polynucleic acid and the second polynucleic acid is performed with the same amplification technique but wherein amplification of the first polynucleic acid and the second polynucleic acid can be controlled by extrinsic conditions.

20. The method of claim 19, wherein amplification of the first polynucleic acid and the second polynucleic acid is performed at different temperatures.

21. The method of claim 20, wherein the primers used for amplification of the first polynucleic acid and the second polynucleic acid have different Tm values.

22. The method of claim 1 for use in diagnostic applications.

23. The method of claim 1 for use in detecting an organism in a sample.

24. The method of claim 1 for use in detecting a microorganism in a sample.

25. A method for determining the presence and/or amount of a first polynucleic acid in a sample comprising subjecting the sample to nucleic acid amplification in which the presence and/or amount of the first nucleic acid is detectable by the presence of a reporter signal generated by polynucleic acid formation from the amplification of the first polynucleic acid, wherein the method comprises nucleic acid amplification of the first polynucleic acid and a second polynucleic acid in the same reaction vessel, the nucleic acid amplification being performed with a predetermined amount of the second polynucleic acid, wherein the product of the amplification of the first polynucleic acid and the product of the amplification of the second polynucleic acid are detected by the same reporter signal, the product of the second polynucleic acid amplification being produced with different reaction kinetics from the product of the amplification of the first polynucleic acid such that the second polynucleic acid acts as an internal control for the method, wherein the reporter signals from amplification of the first polynucleic acid and the second polynucleic acid are detected during the amplification reaction.

26. The method of claim 25 wherein the first polynucleic acid is amplified using exponential nucleic acid amplification and the second polynucleic acid is amplified using non-exponential nucleic amplification.

27. The method of claim 25 wherein the first polynucleic acid is amplified using non-exponential nucleic acid amplification and the second polynucleic acid is amplified using exponential nucleic amplification.

28. A method for determining the presence and/or amount of a first polynucleic acid in a sample comprising subjecting the sample to nucleic acid amplification in which the presence and/or amount of the first nucleic acid is detectable by the presence of a reporter signal generated by polynucleic acid formation from the amplification of the first polynucleic acid, wherein the method comprises nucleic acid amplification of the first polynucleic acid and a second polynucleic acid in the same reaction vessel, the nucleic acid amplification being performed with a predetermined amount of the second polynucleic acid, wherein the product of the amplification of the first polynucleic acid and the product of the amplification of the second polynucleic acid are detected by the same reporter signal, the product of the second polynucleic acid amplification being produced with different reaction kinetics from the product of the amplification of the first polynucleic acid such that the second polynucleic acid acts as an internal control for the method, wherein
  (i) the first polynucleic acid is amplified using exponential nucleic acid amplification and the second polynucleic acid is amplified using non-exponential nucleic acid amplification; or
  (ii) the first polynucleic acid is amplified using non-exponential nucleic acid amplification and the second polynucleic acid is amplified using exponential nucleic acid amplification.

* * * * *

SEQUENCE LISTING

```
<160> NUMBER OF SEQ ID NOS: 10

<210> SEQ ID NO 1
<211> LENGTH: 47
<212> TYPE: DNA
<213> ORGANISM: Artificial Sequence
<220> FEATURE:
<223> OTHER INFORMATION: Primer

<400> SEQUENCE: 1
aaccttgtgg agcatattcg tggttttccg ccattggcga atttatg          47

<210> SEQ ID NO 2
<211> LENGTH: 41
<212> TYPE: DNA
<213> ORGANISM: Artificial Sequence
<220> FEATURE:
<223> OTHER INFORMATION: Primer

<400> SEQUENCE: 2
tctcttggcg cccacaatgt ttttaagcga acgtgtttcc g               41

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
caatggcgcg ttatatttg                                         19

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
```
gagcgcttcc ataattaatt tc                                              22

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
cattactgct cgtaattc                                                   18

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
atatctgaag ttttgcagc                                                  19

<210> SEQ ID NO 7
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 22
<223> OTHER INFORMATION: U = Uracil

<400> SEQUENCE: 7
tgactgaacc agctaagcct guaaaa                                          26

<210> SEQ ID NO 8
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (24)...(24)
<223> OTHER INFORMATION: U = Uracil

<400> SEQUENCE: 8
cgttgctgtg tagctgttaa tacuaaat                                        28

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ataatctact gtttgagatg                                                 20

<210> SEQ ID NO 10
<211> LENGTH: 19
<212> TYPE: DNA
<213> ORGANISM: Artificial Sequence
<220> FEATURE:
<223> OTHER INFORMATION: Primer

```
<400> SEQUENCE: 10
taatgctaag tttcatgtg                                                      19
```